US012258614B2

(12) United States Patent
Lin et al.

(10) Patent No.: US 12,258,614 B2
(45) Date of Patent: *Mar. 25, 2025

(54) HYBRIDIZATION CHAIN REACTION-BASED METHOD FOR AMPLIFYING IMMUNOSIGNALS

(71) Applicant: GenAns Biotechnology Co., Ltd., Beijing (CN)

(72) Inventors: Rui Lin, Beijing (CN); Minmin Luo, Beijing (CN)

(73) Assignee: GenAns Biotechnology Co., Ltd., Beijing (CN)

( * ) Notice: Subject to any disclaimer, the term of this patent is extended or adjusted under 35 U.S.C. 154(b) by 1280 days.

This patent is subject to a terminal disclaimer.

(21) Appl. No.: 16/964,386

(22) PCT Filed: Jan. 26, 2018

(86) PCT No.: PCT/CN2018/074362
§ 371 (c)(1),
(2) Date: Jul. 23, 2020

(87) PCT Pub. No.: WO2019/144389
PCT Pub. Date: Aug. 1, 2019

(65) Prior Publication Data
US 2020/0377926 A1    Dec. 3, 2020

(51) Int. Cl.
*C12Q 1/6804* (2018.01)
*C12Q 1/6818* (2018.01)
*G01N 33/68* (2006.01)

(52) U.S. Cl.
CPC ......... *C12Q 1/6804* (2013.01); *C12Q 1/6818* (2013.01); *G01N 33/6854* (2013.01); *C12Q 2563/107* (2013.01); *G01N 2458/10* (2013.01)

(58) Field of Classification Search
None
See application file for complete search history.

(56) References Cited

U.S. PATENT DOCUMENTS

| 2003/0219803 A1* | 11/2003 | Jayasena | C07H 21/00 435/6.15 |
| 2004/0023207 A1* | 2/2004 | Polansky | A61K 48/005 435/456 |
| 2006/0228733 A1* | 10/2006 | Pierce | C12Q 1/682 536/25.32 |

FOREIGN PATENT DOCUMENTS

| CN | 1417586 A | 5/2003 |
| CN | 106771174 A | 5/2017 |

(Continued)

OTHER PUBLICATIONS

Zhu et al. Ultrasensitive simultaneous detection of four biomarkers based on hybridization chain reaction and biotin-streptavidin signal amplification. Biosensors and Bioelectronics 68:42-48. (Year: 2015).*

(Continued)

*Primary Examiner* — Samuel C Woolwine
(74) *Attorney, Agent, or Firm* — BOND, SCHOENECK & KING, PLLC; George R. McGuire

(57) ABSTRACT

The invention provides an antibody-based bioanalytical method, specifically a hybridization Chain Reaction-based Method for Amplifying Immunosignals named immunosignal HCR (isHCR), which combines antibody-antigen interactions with hybridization Chain Reaction (HCR) technology for amplifying immunosignals. The invention also provides a kit for performing the above isHCR.

21 Claims, 32 Drawing Sheets
Specification includes a Sequence Listing.

(56) References Cited

FOREIGN PATENT DOCUMENTS

| WO | 2015118029 A1 | 8/2015 |
|---|---|---|
| WO | 2017189525 A1 | 11/2017 |

OTHER PUBLICATIONS

Gong et al. Simple method to prepare oligonucleotide-conjugated antibodies and its application to multiplex protein detection in single cells. Bioconjugate Chem 27:217-225. (Year: 2015).*
Choi et al. Immuno-Hybridization Chain Reaction for Enhancing Detection of Individual Cytokine-Secreting Human Peripheral Mononuclear Cells. Anal. Chem. 83:6890-6895. (Year: 2011).*
Yang et al. Graphene Surface-Anchored Fluorescence Sensor for Sensitive Detection of MicroRNA Coupled with Enzyme-Free Signal Amplification of Hybridization Chain Reaction. ACS Appl. Mater. Interfaces 4:6450-6453. (Year: 2012).*
Molecular Probes Handbook, Chapter 7, Section 7.4, Anti-Dye and Anti-Hapten Antibodies, pp. 272-276. (Year: 2010).*
Harry M. T. Choi, et al. "Next-Generation in Situ Hybridization Chain Reaction: Higher Gain, Lower Cost, Great Durability" ACS NANO, vol. 8, No. 5, Apr. 8, 2014 (Apr. 8, 2014), pp. 4284-4294.
International Search Report and Non-Translated Written Opinion Form PCT/IS/210 and PCT/ISA/237, International Application No. PCT/CN2018/074362 pp. 1-8, International Filing Date Jan. 26, 2018 mailing date of search report Oct. 29, 2018.
Harry M. T. Choi et al. "Next-Generation in Situ Hybridization Chain Reaction: Higher Gain, Lower Cost, Greater Durability" ACS NANO, vol. 8, No. 5, Apr. 8, 2014 (Apr. 8, 2014), pp. 4284-4294.
Wang C K, Wang Q Q, and Chen D. Research Progress of "hairpin" structured DNA for bioanalysis sensor. Chinese Chemical Bulletin 80.5(2017):8.
First Office Action issued by the Chinese Patent Office on Mar. 30, 2022.
Second Office Action issued by the Chinese Patent Office on Apr. 14, 2023.
Notification Of Granting Invention Patent Right issued by the Chinese Patent Office on Apr. 14, 2023.

* cited by examiner c      SA-546      isHCR-546

SEQUENCE LISTING

<160> NUMBER OF SEQ ID NOS: 6

<210> SEQ ID NO 1
<211> LENGTH: 41
<212> TYPE: DNA
<213> ORGANISM: Artificial Sequence
<220> FEATURE:
<223> OTHER INFORMATION: Synthesized Probe

<400> SEQUENCE: 1
atatagcatt ctttcttgag gagggcagca aacgggaaga g           41

<210> SEQ ID NO 2
<211> LENGTH: 72
<212> TYPE: DNA
<213> ORGANISM: Artificial Sequence
<220> FEATURE:
<223> OTHER INFORMATION: Synthesized Amplifier

<400> SEQUENCE: 2
cgtaaaggaa gactcttccc gtttgctgcc ctcctcgcat tctttcttga ggagggcagc    60
aaacgggaag ag                                                       72

<210> SEQ ID NO 3
<211> LENGTH: 72
<212> TYPE: DNA
<213> ORGANISM: Artificial Sequence
<220> FEATURE:
<223> OTHER INFORMATION: Synthesized Amplifier

<400> SEQUENCE: 3
gaggagggca gcaaacggga agagtcttcc tttacgctct tcccgtttgc tgccctcctc    60
aagaaagaat gc                                                       72

<210> SEQ ID NO 4
<211> LENGTH: 41
<212> TYPE: DNA
<213> ORGANISM: Artificial Sequence
<220> FEATURE:
<223> OTHER INFORMATION: Synethesized Probe

<400> SEQUENCE: 4
atatacactt catatcactc actcccaatc tctatctacc c           41

<210> SEQ ID NO 5
<211> LENGTH: 72
<212> TYPE: DNA
<213> ORGANISM: Artificial Sequence
<220> FEATURE:
<223> OTHER INFORMATION: Synthesized Amplifier

<400> SEQUENCE: 5
attggatttg tagggtagat agagattggg agtgagcact tcatatcact cactcccaat    60
ctctatctac cc                                                       72

<210> SEQ ID NO 6
<211> LENGTH: 72
<212> TYPE: DNA
<213> ORGANISM: Artificial Sequence
<220> FEATURE:
<223> OTHER INFORMATION: Synthesized Amplifier -continued

```
<400> SEQUENCE: 6
ctcactccca atctctatct accctacaaa tccaatgggt agatagagat tgggagtgag      60
tgatatgaag tg                                                         72
```

HYBRIDIZATION CHAIN REACTION-BASED METHOD FOR AMPLIFYING IMMUNOSIGNALS

CROSS-REFERENCE TO RELATED APPLICATION

The present application is the United States National Phase application of PCT Application PCT/CN2018/074362, filed Jan. 26, 2018, the entirety of which is incorporated herein by reference.

BACKGROUND

Owing to their ease of use, speed, and cost effectiveness, antibody-based immunoassays remain the most popular methods for detecting and identifying the location of proteins and other biomolecules in biological samples. These methods use a primary antibody that binds selectively to a target molecule (antigen), and this antibody-antigen interaction can be visualized via a conjugated reporter or a labeled secondary antibody that can recognize and react with the primary antibody-epitope complex (Han, K. N., Li, C. A. & Seong, G. H. Annu. Rev. Anal. Chem. 6, 119-141 (2013)). A major limitation in the use of immunoassays is that the low abundance of a given target molecule in a sample often necessitates signal amplification before detection is possible. Amplification can be achieved using conjugated enzymes such as horseradish peroxidase (HRP) and alkaline phosphatase, which catalyze the deposition of chromogenic substrates on target complexes (Bobrow, M. N., Harris, T. D., Shaughnessy, K. J. & Litt, G. J. J. Immunol. Methods 125, 279-285 (1989)). Fluorogenic substrates, especially those based on HRP-tyramide reaction chemistries, have been developed to support high-resolution fluorescence microscopy (Stack, E. C., Wang, C., Roman, K. A. & Hoyt, C. C. Methods 70, 46-58 (2014)). Although very useful and widely-employed, current amplification methods have several drawbacks: they often generate high background, they can reduce spatial resolution due to dye diffusion, they are difficult to use for the simultaneous detection of multiple amplified signals (Carvajal-Hausdorf, D. E., Schalper, K. A., Neumeister, V. M. & Rimm, D. L. Lab. Invest. 95, 385-396 (2015)), and they are unsuitable for use with large-volume samples in several powerful new tissue expansion and clearing techniques.

In this invention, we find that an enzyme-free amplification approach could overcome many of these limitations. In particular, hybridization chain reaction (HCR) technology is adapted to amplify immunosignals. HCR, which is based on recognition and hybridization events that occur between sets of DNA hairpin oligomers that self-assemble into polymers, has to date been used primarily for the amplification of mRNA signals from in situ hybridization samples (Choi, H. M. T., Beck, V. A. & Pierce, N. A. ACS Nano 8, 4284-4294 (2014); Shah, S. et al. Development 143, 2862-2867 (2016)), and more recently for the detection of protein-protein interactions (Koos, B. et al. Nat. Commun. 6, 7294 (2015)). In a typical usage case, nucleic acid probes complementary to the target mRNA molecule are used as 'initiator' oligos. Starting from the initiator oligos, a series of polymerization reactions are used to add fluorophore-labeled nucleic acid 'amplifier' oligos to the target mRNA-initiator complex; the fluorophores are then visualized.

SUMMARY OF THE INVENTION

The invention provides an antibody-based bioanalytical method, specifically a method named immunosignal HCR (isHCR), which combines antibody-antigen interactions with hybridization Chain Reaction (HCR) technology. The invention also provides a kit for performing the above isHCR. The invention further provides an antibody-based bioanalytical method, specifically a method named multi-round immunosignal HCR (isHCR) (multi-round isHCR), which combines antibody-antigen interactions with hybridization Chain Reaction (HCR), wherein multiple amplification rounds are used to branch and grow the HCR polymers. Correspondingly, the invention also provides a kit for performing multi-round isHCR.

In the first aspect, the invention provides an isHCR method, which comprises conjugating a HCR initiator to an antibody (including but not limited to a traditional IgG and a nanobody) specific to an analyte, and adding a pair of amplifiers to conduct a hybridization chain reaction.

In the second aspect, the invention provides a kit for performing the isHCR method, which comprises (1) an antibody specific to an analyte; (a) a HCR initiator; and (3) a pair of HCR amplifiers, wherein the HCR initiator has a region for hybridizing with a HCR amplifier, and a region for conjugating the antibody.

In the third aspect, the invention provides a HCR initiator, having a region for hybridizing with HCR amplifiers and a region for conjugating an antibody specific to an analyte to be analyzed.

In the fourth aspect, the invention provides an antibody specific to an analyte to be analyzed, which is directly or indirectly conjugated to a HCR initiator.

The HCR initiators can be hybridized with any of several types of self-assembling DNA HCR amplifiers, including a fluorophore-labeled amplifier oligo that can be used for visualization of the original target signal.

The amplifiers are fluorophore-tagged amplifiers or biotinylated HCR amplifiers.

HCR initiators are conjugated to antibodies using many interactions, such as the streptavidin-biotin interaction, covalent bond interaction (chemical linkers, e.g., amine-reactive linkers, thiol-reactive linkers or click chemistry linkers), and etc. The amine-reactive linkers can be linkers containing succinimidyl ester group. The thiol-reactive linkers can be linkers containing maleimide group. The click chemistry linkers can be linkers containing click chemistry functional groups, such as NHS-Azide linkes, NHS-DBCO linkers, maleimide-azide linkers, or maleimide-DBCO linkers.

Preferably, the HCR initiator is a biotinylated initiator, which is capable of attaching to the vacant binding sites of streptavidin, and the streptavidin is capable of attaching to a biotinylated antibody, and whereby the HCR initiator is conjugated to the antibody.

Preferably, the HCR initiators and amplifiers (H1 and H2) used in the present isHCR method can be terminally modified or internally modified for improving the signal strength or as an interface to access other chemical reactions. The HCR initiators and amplifiers (H1 and H2) used in the present isHCR method can be terminally modified or internally modified with chemical groups and/or fluorescent dyes. For example, the HCR initiators and amplifiers (H1 and H2) used in the present isHCR method can be terminally modified and/or internally modified with biotin, acrydite, amine, thiol, DBCO, and/or fluorescent dye. The fluorescent dye may be FITC, Cyanine dyes, Alexa Fluors, Dylight fluors, Atto dyes or Janelia Fluor dyes.

Preferably, the isHCR method uses biotin-streptavidin interaction, wherein DNA-biotin HCR initiator is attached to a biotinylated antibody and in turn trigger the self-assembly of labeled HCR amplifiers into polymers. For example, the labeled HCR amplifiers are fluorophore labeled HCR amplifiers.

The isHCR method uses label-free streptavidin, which allows the attachment of synthesized 5'-biotinylated DNA HCR initiators to the vacant binding sites of streptavidin, which is attached to the biotinylated antibody.

The biotinylated antibody can be a biotinylated secondary antibody that reacts with a primary antibody specific to a target antigen.

Preferably, the present invention provides a kit, which comprises: (1) a biotinylated antibody specific to an analyte; (2) streptavidin; (3) a biotinylated initiator; and (4) a pair of HCR amplifiers.

The present isHCR method or kit can be used to powerfully amplify immunosignals at different subcellular locations (e.g., cell and vesicle membrane, cytosol, mitochondrion, and cell nucleus) and in various types of samples (e.g., blotting, cultured cells, tissue sections, and whole organ). Therefore, the isHCR method can be used to analyze an analyte in a biological sample. In particular, the present isHCR method is useful for laboratory, clinical or diagnostic application, especially, on site application, for example the clinical point care.

The isHCR method is especially useful in applications that require sensitive detection of immunosignals. We here demonstrated its use for amplifying immunosignals with monoclonal antibodies, and for detecting the extremely low-abundance signal of translocated bacterial effectors, among other applications. The actual amplification performance of isHCR depends on the particular applications and on the abundance of a given target signal: for signal amplification in western blotting and tissue section samples, isHCR outperformed standard IHC by up to 2 orders of magnitude.

In the fifth aspect, the invention provides a multi-round isHCR method, which comprises conjugating a HCR initiator to an antibody (including but not limited to traditional IgGs and nanobodies) specific to an analyte, and adding a pair of amplifiers to conduct a hybridization chain reaction, wherein an amplifier or a pair of amplifiers are modified to access branched multiple-round amplification in order to branch and grow the HCR polymers.

In the sixth aspect, the invention provides a kit for performing multi-round isHCR, which comprises (1) an antibody specific to an analyte; (a) a HCR initiator; and (3) a pair of HCR amplifiers, wherein the HCR initiator has a region for hybridizing with a HCR amplifier, and a region for conjugating the antibody, and an amplifier or a pair of amplifiers are modified to access branched multiple-round amplification in order to branch and grow the HCR polymers.

In the seventh aspect, the invention provides a pair of amplifiers, wherein an amplifier or a pair of amplifiers are modified to access branched multiple-round amplification in order to branch and grow the HCR polymers.

The HCR initiators can be hybridized with any of several types of self-assembling DNA HCR amplifiers, including a fluorophore-labeled amplifier oligo that can be used for visualization of the original target signal.

HCR initiators are conjugated to antibodies using many interactions, such as the streptavidin-biotin interaction, covalent bond interaction (chemical linkers, e.g., amine-reactive linkers or click chemistry linkers), and etc. The amine-reactive linkers can be linkers containing the succinimidyl ester group. The click chemistry linkers can be linkers containing click chemistry functional groups, such as NHS Azide linkes, NHS-DBCO linkers, maleimide-azide linkers, or maleimide-DBCO linkers.

Preferably, the HCR initiator is a biotinylated initiator, which is capable of attaching to the vacant binding sites of streptavidin, and the streptavidin is capable of attaching to a biotinylated antibody, and whereby the HCR initiator is conjugated to the antibody.

The HCR initiators/or and amplifiers (H1 and H2) used in the present multi-round isHCR can be terminally modified or internally modified for improving the signal strength or as an interface to access other chemical reactions.

The HCR amplifiers (H1 and H2) used in the present multi-round isHCR can be terminally modified or internally modified with chemical groups and/or fluorescent dyes, which allows initiating further rounds of amplification. In this situation, the amplifiers (H1 and H2) can be terminally modified or internally modified with biotin, digoxigenin, acrydite, amine, succinimidyl ester, thiol, azide, TCO, Tetrazine, Alkyne, and/or DBCO. Fluorescent dye, such as FITC, Cyanine dyes, Alexa Fluors, Dylight fluors, Atto dyes or Janelia Fluor dyes, wherein the Alexa Fluors can be for example Alexa Fluro 546, Alexa Fluor 488, and/or Alexa Fluor 647, can be also tagged to the amplifiers together with biotin, digoxigenin, acrydite, amine, succinimidyl ester, thiol, azide, TCO, Tetrazine, Alkyne, and/or DBCO. For example, amplifiers can be labeled with bitoin groups. Once these DNA-biotin amplifiers have self-assembled and joined the growing isHCR polymer, their biotins can be reacted with newly-added streptavidins (and hence can be reacted with more HCR initiators, etc.), thereby initiating further rounds of polymer elaboration. A pair of signal molecule-modified amplifiers (e.g., a pair of fluorophore-tagged amplifiers) can be added to the final round of isHCR" for visualization.

Preferably, the amplifiers are modified at internal positions, which are more accessible to the binding partners, such as streptavidins, which serve as anchors for each successive round of branching in multi-round isHCR (isHCR").

The HCR initiators used in the present multi-round isHCR method can be terminally modified or internally modified for improving the signal strength. The HCR initiators used in the present multi-round isHCR method can be terminally modified or internally modified with chemical groups and/or fluorescent dyes. For example, the HCR initiators used in the present multi-round isHCR can be terminally modified and/or internally modified with biotin, acrydite, amine, thiol, DBCO, and/or fluorescent dye. The fluorescent dye may be FITC, Cyanine dyes, Alexa Fluors, Dylight fluors, Atto dyes or Janelia Fluor dyes, wherein the Alexa Fluors can be for example Alexa Fluro 546, Alexa Fluor 488, or Alexa Fluor 647.

Preferably, the multi-round isHCR uses biotin-streptavidin interaction, wherein DNA-biotin HCR initiator is attached to a biotinylated antibody and in turn trigger the self-assembly of labeled DNA HCR amplifiers into polymers. For example, the labeled HCR amplifiers are fluorophore labeled HCR amplifiers.

The multi-round isHCR uses label-free streptavidin, which allows the attachment of synthesized 5'-biotinylated DNA HCR initiators to the vacant binding sites of streptavidin, which is attached to the biotinylated antibody.

The biotinylated antibody can be a biotinylated secondary antibody that reacts with a primary antibody specific to a target antigen.

The multi-round isHCR can be used to powerfully amplify immunosignals at different subcellular locations (e.g., cell and vesicle membrane, cytosol, mitochondrion, and cell nucleus) and in various types of samples (e.g., blotting, cultured cells, tissue sections, and whole organ). Therefore, the isHCR method can be used to analyze an analyte in a biological sample. In particular, the present isHCR method is useful for laboratory, clinical or diagnostic application, especially, on site application, for example the clinical point care.

The multi-round isHCR is especially useful in applications that require sensitive detection of immunosignals. The isHCR method can be used for amplifying immunosignals with monoclonal antibodies, for detecting the extremely low-abundance signal of translocated bacterial effectors, and for enhancing diluted immunosignals in ExM, among other applications. The actual amplification performance of isHCR depends on the particular applications and on the abundance of a given target signal: for signal amplification in western blotting and tissue section samples, isHCR outperformed standard IHC by up to 2 orders of magnitude; improvements of 3 orders of magnitude were achieved with ExM samples. Compared with non-multi-round isHCR, tests based on western blotting of HA-tagged scFv revealed that two extra rounds of amplification (isHCR$^3$) resulted in an additional ten-fold improvement in protein-detection sensitivity. When we tested the performance of isHCR″ for immunostaining against TH, the immunopositive signal intensity increased with each round of isHCR amplification.

In the eighth aspect, the invention provides an improved isHCR method or an improved isHCR″ method for amplifying immunofluorescence with lower background, which in addition to the above isHCR or isHCR″, further comprises using grapheme oxide (GO) to absorb unassembled HCR amplifiers. If the amplifiers are terminally modified and/or internally modified with fluorescent dye, grapheme oxide (GO) may also quench the fluorescence.

In the ninth aspect, the invention provides a kit for performing the improved isHCR method, which comprises: (1) an antibody specific to an analyte; (a) a HCR initiator; (3) a pair of HCR amplifiers, wherein the HCR initiator has a region for hybridizing with a HCR amplifier, and a region for conjugating the antibody; and (4) grapheme oxide (GO).

In the tenth aspect, the invention provides a kit for performing the improved multi-round isHCR, which comprises (1) an antibody specific to an analyte; (a) a HCR initiator; and (3) a pair of HCR amplifiers, wherein the HCR initiator has a region for hybridizing with a HCR amplifier, and a region for conjugating the antibody, and an amplifier or a pair of amplifiers are modified to access branched multiple-round amplification in order to branch and grow the HCR polymers; and (4) grapheme oxide (GO).

Graphene Oxide in the present invention has a particle size of <500 nm. Crucially, in addition to abolishing the fluorescence of HCR amplifiers, the addition of HCR initiators along with HCR amplifiers and GO resulted in substantial recovery of fluorescence, likely because the initiators triggered the formation of double-strand-nicked polymers of HCR amplifiers, thereby protecting them from the adsorption activity of GO. That is, GO can be used to suppress background levels, further enhancing the performance of isHCR.

The addition of GO reduced the background but did not diminish the signal intensity, resulting in an improved signal-to-noise ratio as compared to isHCR amplification without GO. Surprisingly, further analysis using antibody serial dilution experiments showed that isHCR with GO significantly increased signal intensity as compared to a standard IHC staining method, achieving a greater than 80× amplification factor when the primary antibody was highly diluted.

The invention encompasses all combination of the particular embodiments recited herein.

DESCRIPTION OF PARTICULAR
EMBODIMENTS OF THE INVENTION

In the first embodiment, the inventors used isHCR to analyze a purified HA-tagged protein with typical western blotting methods. The analyte protein was a purified single-chain variable fragment (scFv) (Tanenbaum, M. E., Gilbert, L. A., Qi, L. S., Weissman, J. S., and Vale, R. D. Cell 159, 635-646.(2014)), and these experiments used DNA-Alexa Fluor 546 HCR amplifiers (HCR-546). The isHCR-amplified fluorescence signal for 1 ng of scFv was comparable in strength to the fluorescence signal for 100 ng of scFv as measured with a traditional Alexa Fluor 546-conjugated streptavidin method (SA-546), indicating that isHCR can produce a 100-fold increase in protein-detection sensitivity (FIG. 1b). In comparison to a popular commercially-available enzyme-based chemiluminescent detection method, isHCR exhibited similar detection sensitivity, but had a broader dynamic range (FIG. 2).

Figure 3A:
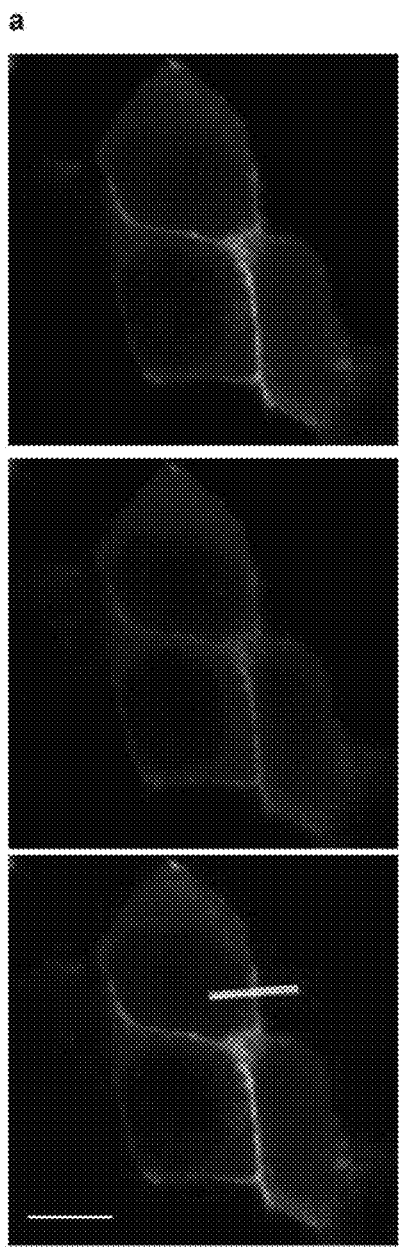
FIG. 3. isHCR amplification maintains the spatial resolution of membrane-bound GFP (mGFP) immunosignals in cultured cells.
Figure 3B:
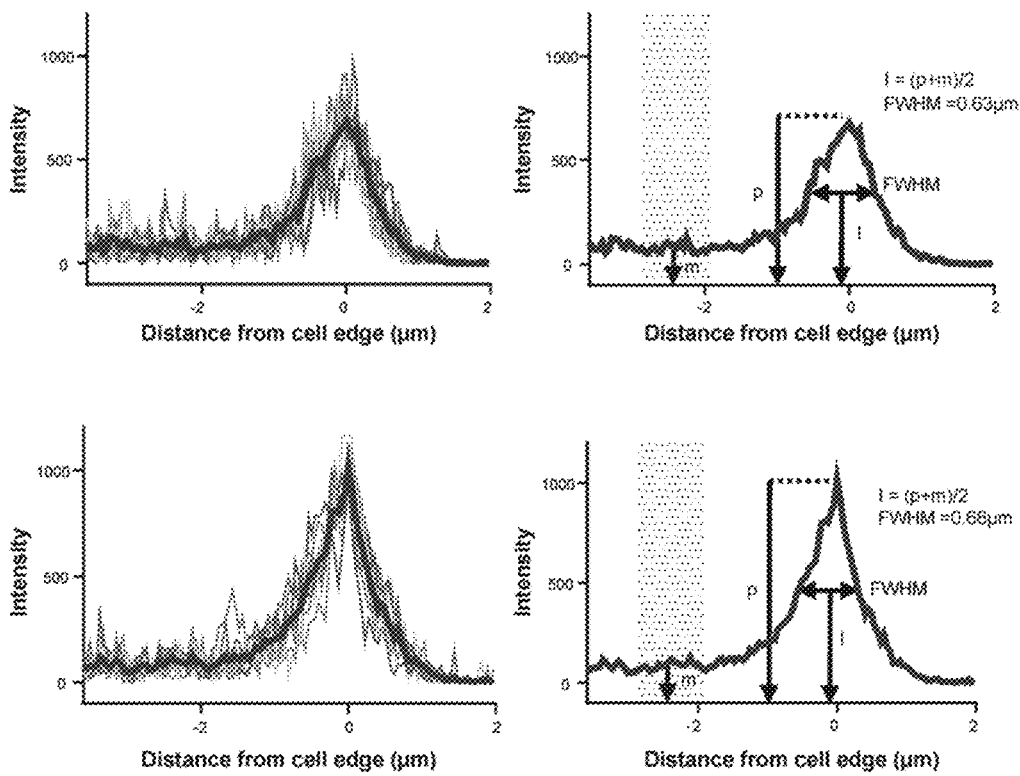

Then, in the second embodiment, the inventors next examined its performance in cells. Cultured HEK293T cells expressing membrane-bound enhanced GFP (mGFP) were immunostained against GFP. The immunosignal was amplified via isHCR using DNA-fluorophore HCR amplifiers. The isHCR-amplified fluorescence signal for the target was dramatically stronger than the signal measured with a typical fluorophore-conjugated streptavidin method (FIG. 1c). To confirm the specificity of isHCR amplification, additional control experiments and analyses with mGFP-expressing cells were performed. An antibody mixture containing equal amounts of Alexa Fluor 488-conjugated secondary antibodies and biotinylated secondary antibodies were used for the detection of anti-GFP primary antibodies, and the signals for the biotinylated secondary antibodies were amplified using isHCR-546. Confocal microscopy showed that unamplified and amplified signals were colocalized, indicating that isHCR amplified the true mGFP signal (FIG. 3a). Moreover, these experiments confirmed that isHCR does not affect the spatial resolution of diffraction-limited confocal imaging at the subcellular level: the mean width of cell membranes as calculated from the unamplified mGFP signal data did not differ from the mean width calculated from isHCR-amplified mGFP signal data (FIG. 3b, c).

Figure 4A:
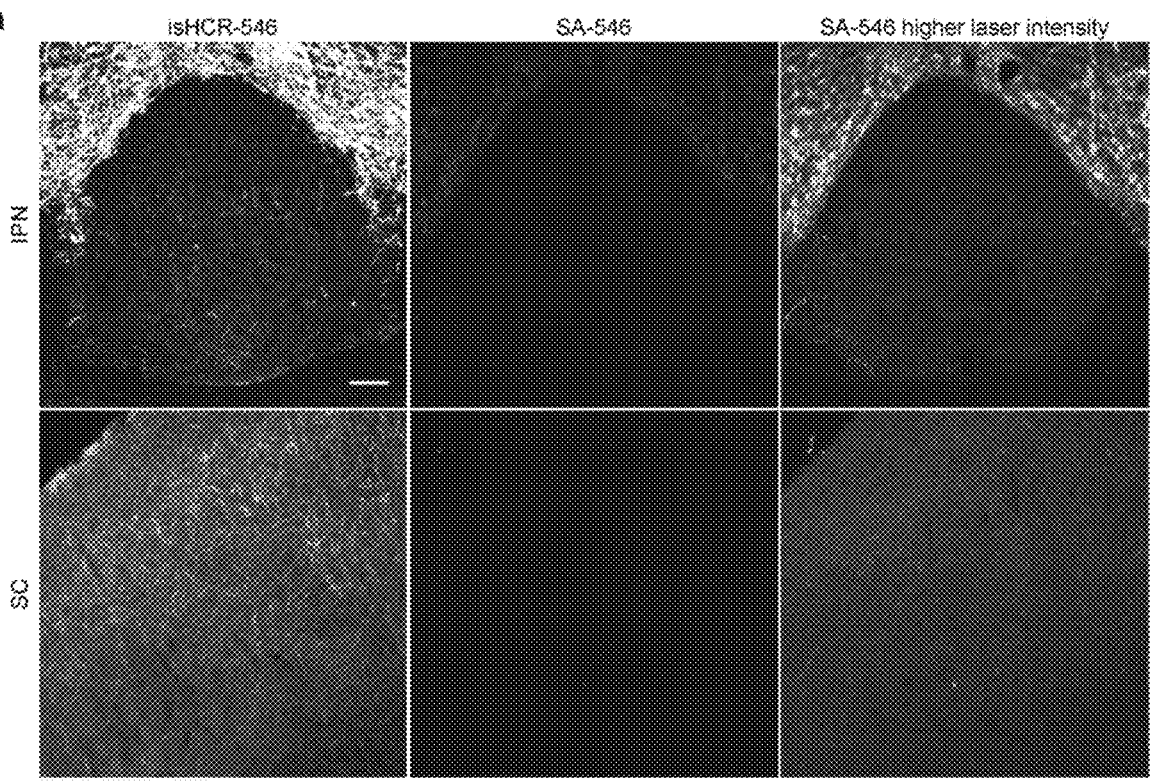
FIG. 4. TH immunostaining using isHCR reveals much richer catecholaminergic innervations in the brain.
Figure 4B:
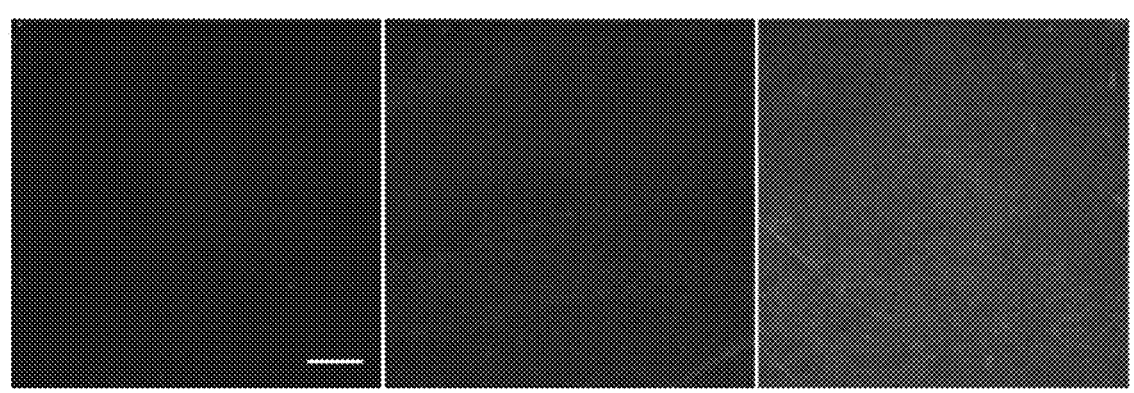
Figure 4C:
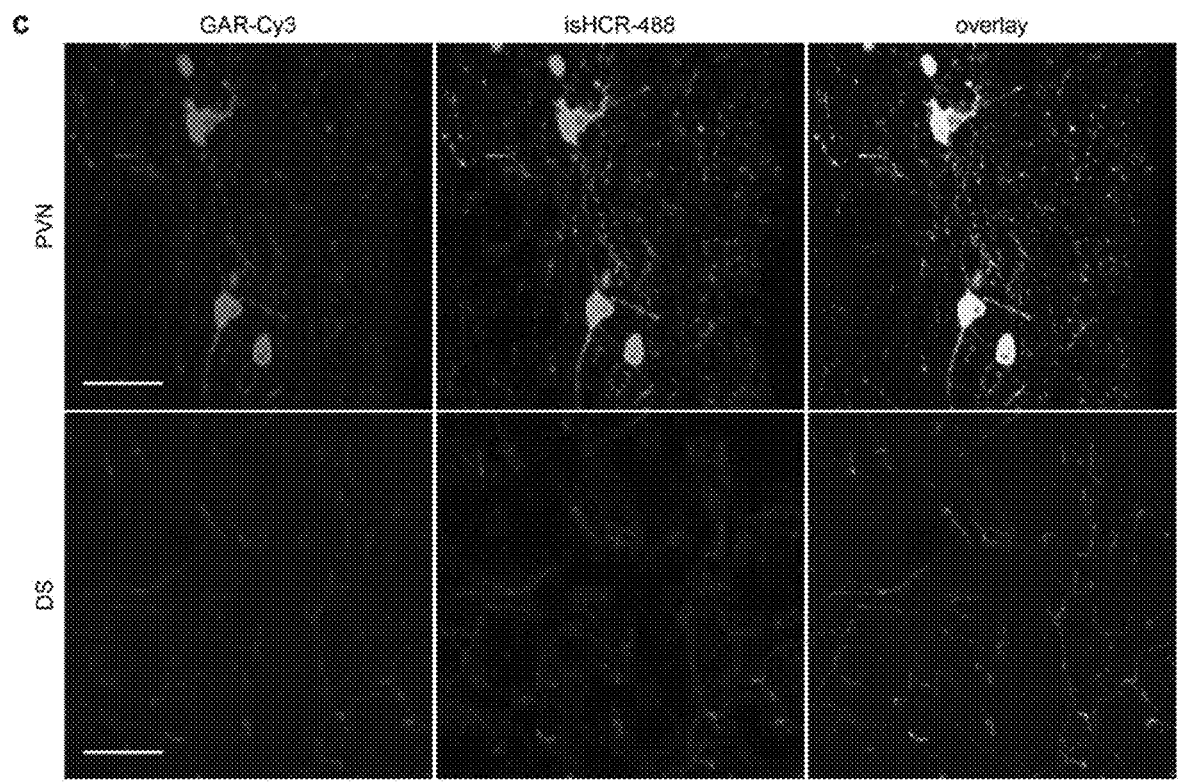

In the third embodiment, isHCR was applied to enhance immunohistochemistry (IHC) staining signals in tissues. Mouse brain sections were immunostained against tyrosine hydroxylase (TH), a key enzyme for catecholamine biosynthesis. Compared to a traditional fluorophore-conjugated streptavidin method carried out in parallel, our isHCR analysis revealed a more widespread distribution of TH-positive signals in neuronal processes throughout the brain. In addition to the strong signals that were visible with both methods, isHCR amplification revealed numerous discrete TH-positive neuronal processes in the cortex and subcortical structures; TH-positive signals for these processes were very weak or negligible in the traditional immunostaining analysis (FIG. 1d and FIG. 4a). Omitting the primary antibody against TH produced no specific labeling in the brain (FIG. 4b). Additional control TH-immunostaining experiments on two brain areas showed strong TH signals in the traditional IHC analysis: the dorsal striatum (DS) and the periventricular nucleus (PVN) (FIG. 1e and FIG. 4c). For both brain regions, the unamplified and isHCR-amplified signals were colocalized, and no significant difference was observed in the mean width of TH-positive neuronal processes (FIG. 1e and FIG. 4c), further confirming the specificity of isHCR amplification and showing that isHCR amplification does not affect the spatial resolution of diffraction-limited confocal imaging at the cellular and sub-cellular level.

Considering the vast number of biotinylated antibodies (secondary antibodies and monoclonal primary antibodies) that are commercially available, the compatibility isHCR with the streptavidin-biotin interaction will allow rapid adoption of isHCR as an optional "add-on" amplification step for most existing immunoassays. The streptavidin-biotin version of isHCR will also likely be used in combination with other protein-streptavidin technologies (e.g., Strep-tags and in vivo biotinylation using biotin ligases).

These direct conjugation strategies will reduce the size of isHCR amplification complexes, and thereby likely facilitate the use of isHCR in large-volume samples and in high-resolution imaging. All of the required reagents for isHCR are commercially available and are very affordable. Considering the vast expanse of biotechnologies (e.g., protein tags, DNA modifications, reaction chemistries, etc.) that can potentially be incorporated into isHCR, it is conceivable that a great many biosensors and antibody-based methods in life science research could be improved or extended via the creative application of these methods.

Figure 5A:
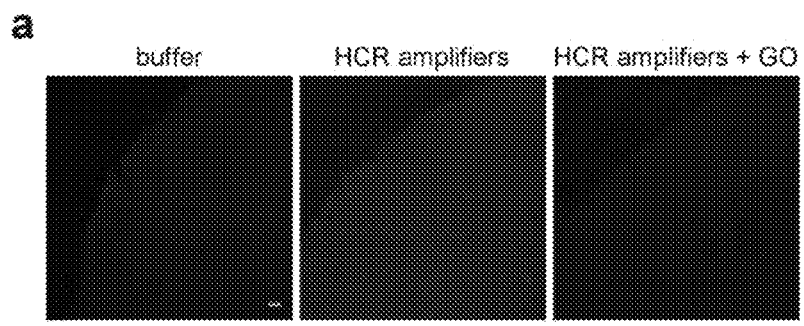
FIG. 5. Optimization of isHCR that reduces background noise.

Despite the impressive performance of isHCR in immunosignal amplification in western blotting, cultured cells, and tissue section applications, the inventors noted that in brain sections isHCR produced higher background than the traditional fluorescence IHC (FIG. 5a and FIG. 4a, b). Incubating brain sections with DNA-fluorophore HCR amplifiers alone resulted in high background levels, even after extensive washing (FIG. 5a), suggesting that unassembled HCR amplifiers in tissue sections contribute to the high background levels we observed. Considering that a reduction in background intensity would be expected to improve the signal-to-noise ratio, ways to modify the isHCR process to suppress background fluorescence were explored.

Figure 12A:
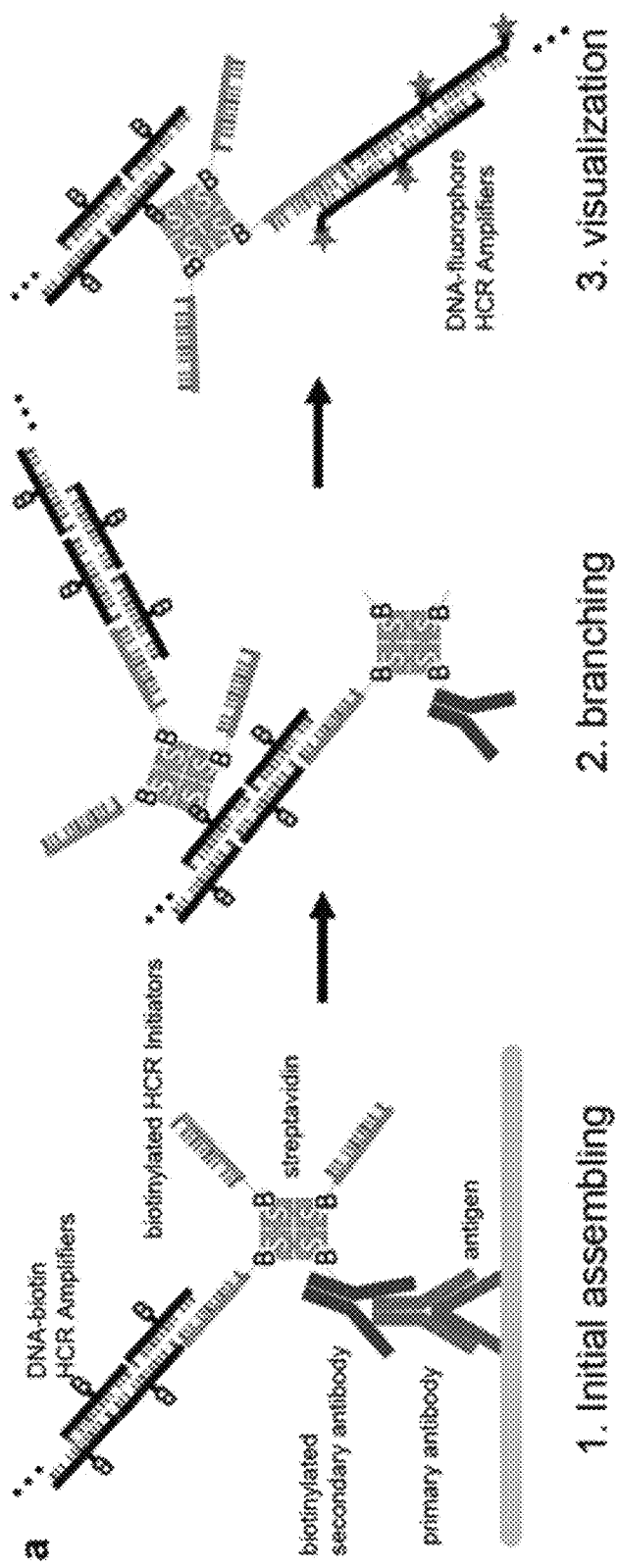
FIG. 12. Multi-round amplification using isHCR″.
Figure 12B:
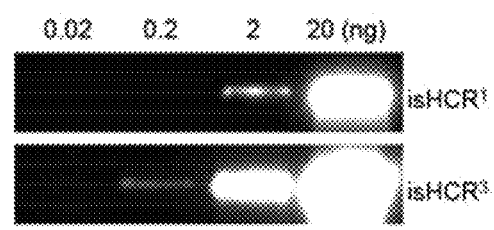

In the fourth embodiment, HCR initiators were reacted with DNA-biotin amplifiers. Once these DNA-biotin amplifiers have self-assembled and joined the growing isHCR polymer, their biotins can be reacted with newly-added streptavidins (and hence more HCR initiators, etc.), thereby initiating further rounds of polymer elaboration (FIG. 12a). The final round of isHCR$^n$ should add amplifiers for visualization (e.g., DNA-fluorophore amplifiers). Tests based on western blotting of HA-tagged scFv revealed that two extra rounds of amplification (isHCR$^3$) resulted in an additional ten-fold improvement in protein-detection sensitivity (FIG. 12b).

Figure 12C:
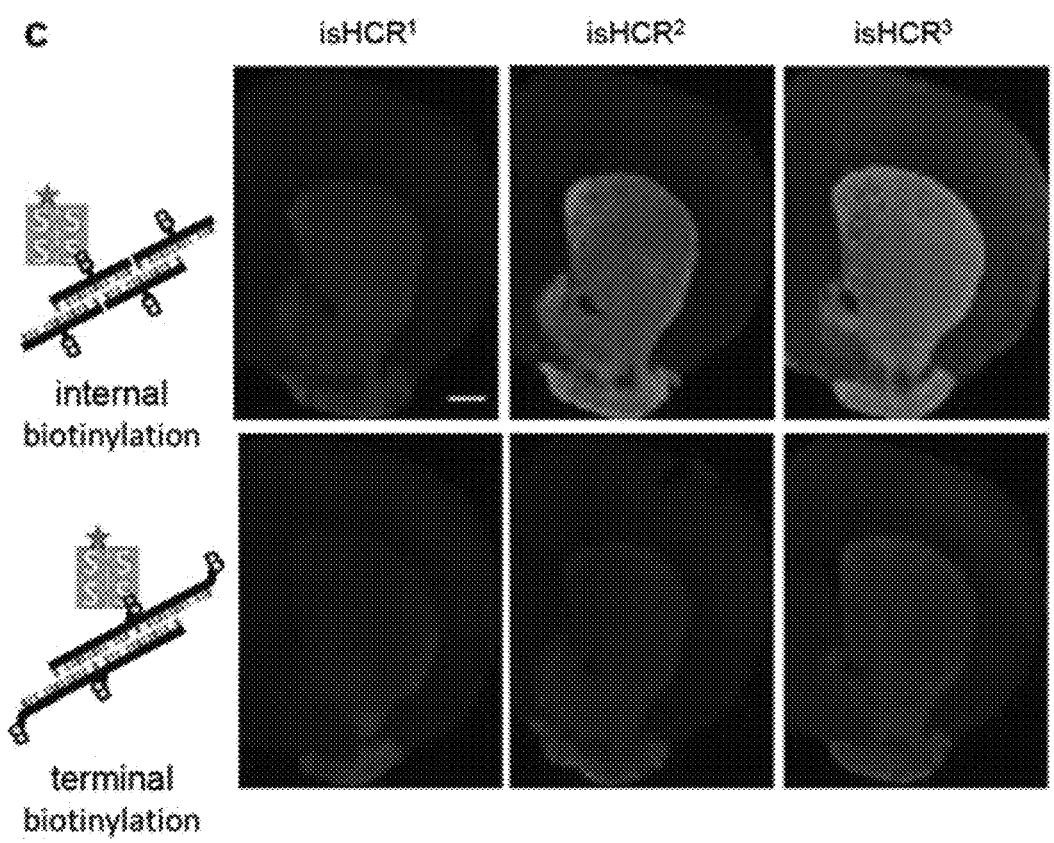

In the fifth embodiment, we tested the performance of isHCR$^n$ for immunostaining against TH, the immunopositive signal intensity increased with each round of isHCR amplification (FIG. 12c).

In addition, in this embodiment, we found the biotinylation position is critically important in determining amplification efficiency. Compared to amplifiers with biotins at their terminal ends, amplifiers with biotin groups at internal positions are more accessible to streptavidins, which serve as anchors for each successive round of branching in isHCR$^n$ (FIG. 12c).

Figure 12D:
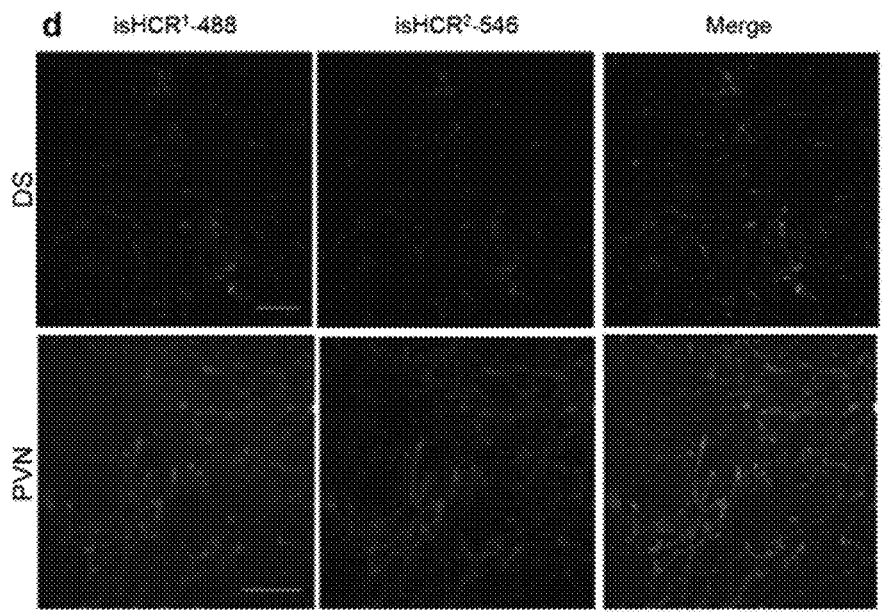
Figure 12E:
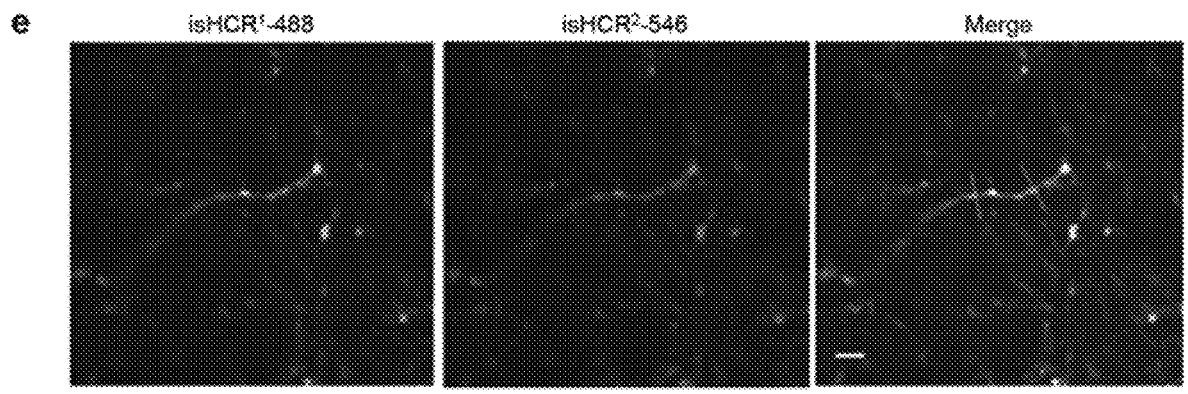
Figure 12E:
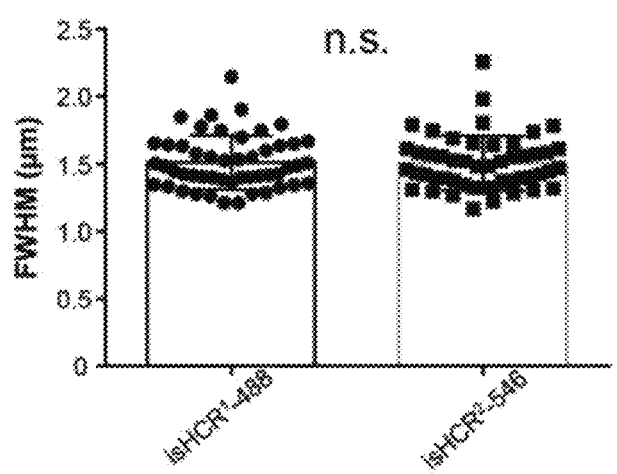
Figure 12F:
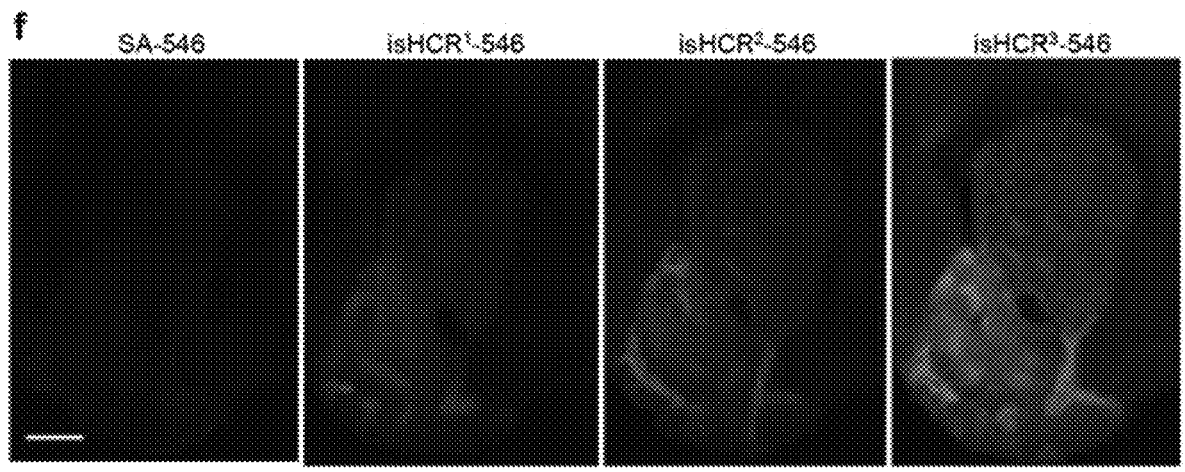
Figure 12G:
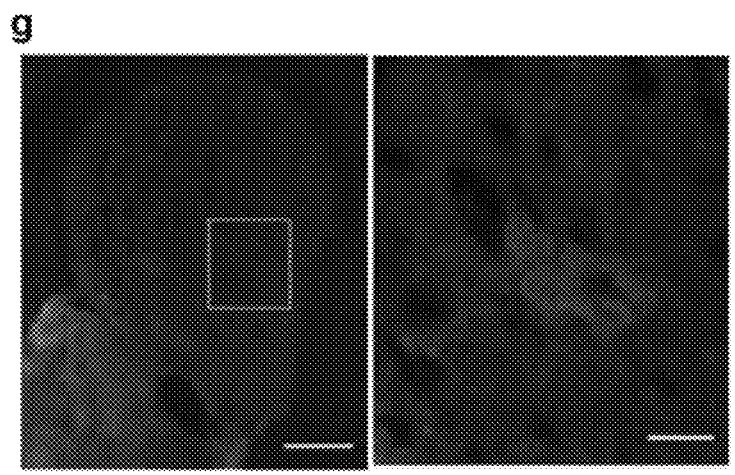

Control experiments confirmed that the specificity and optical resolution were retained over multiple rounds of isHCR$^n$ amplification (FIG. 12d, e). Further tests showed that the immunosignals of the neuropeptide substance P were progressively amplified by three rounds of isHCR, which upon isHCR$^3$ revealed rich substance P expression in neuronal processes in both the striatum and the basal forebrain (FIG. 12f, g).

Figure 5B:
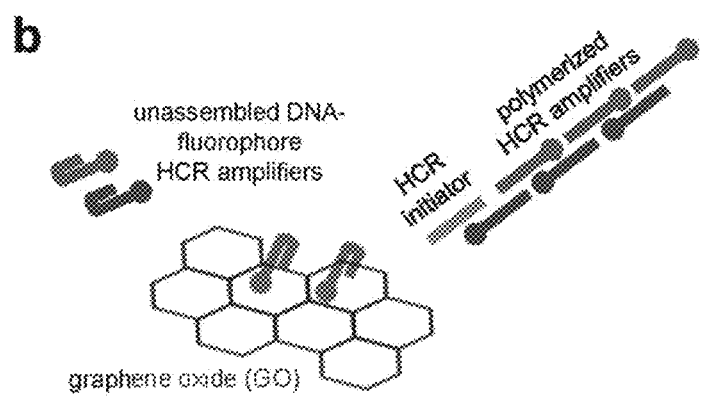
Figure 5C:
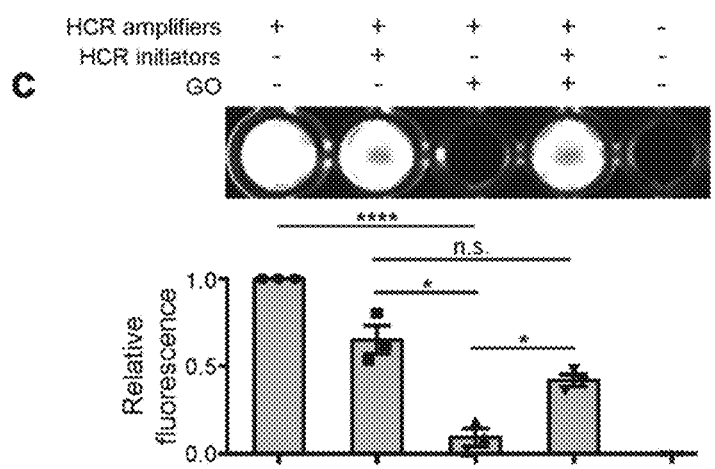
Figure 5D:
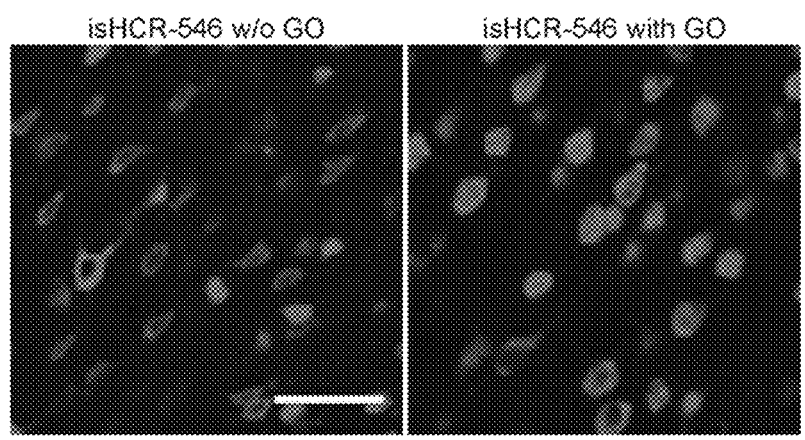
Figure 5D:
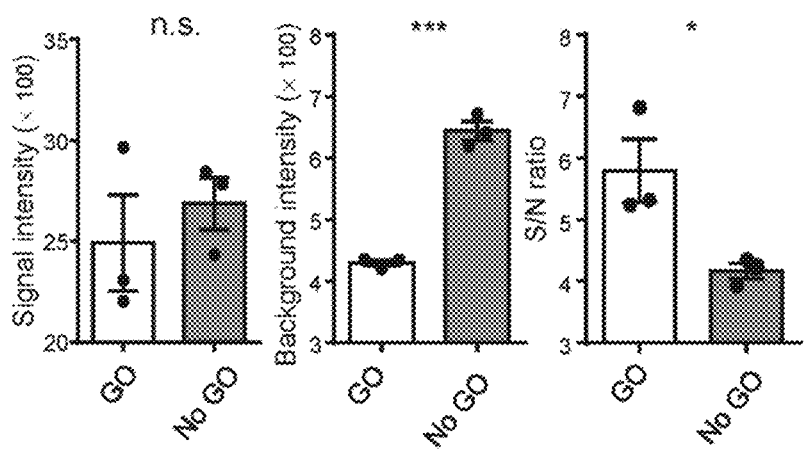

In the sixth embodiment, GO is used to adsorb unassembled HCR amplifiers and thereby quench their fluorescence (FIG. 5b). In microplate wells, GO completely abolished the fluorescence of HCR amplifiers (FIG. 5c). Crucially, the addition of HCR initiators along with HCR amplifiers and GO resulted in substantial recovery of fluorescence, likely because the initiators triggered the formation of double-strand-nicked polymers of HCR amplifiers, thereby protecting them from the adsorption activity of GO (FIG. 5c). In brain sections, the application of a mixture of GO and DNA-fluorophore HCR amplifiers produced substantially lower background fluorescence levels compared to DNA-fluorophore HCR amplifiers alone (FIG. 5a). We immunostained brain sections against NeuN to quantitatively assess the effect of GO on isHCR amplification in tissue samples. The addition of GO reduced the background but did not diminish the signal intensity, resulting in an improved signal-to-noise ratio as compared to isHCR amplification without GO (FIG. 5d). Further analysis using antibody serial dilution experiments showed that isHCR with GO significantly increased signal intensity as compared to a standard IHC staining method, achieving a greater than 80× amplification factor when the primary antibody was highly diluted (FIG. 6).

Figure 5E:
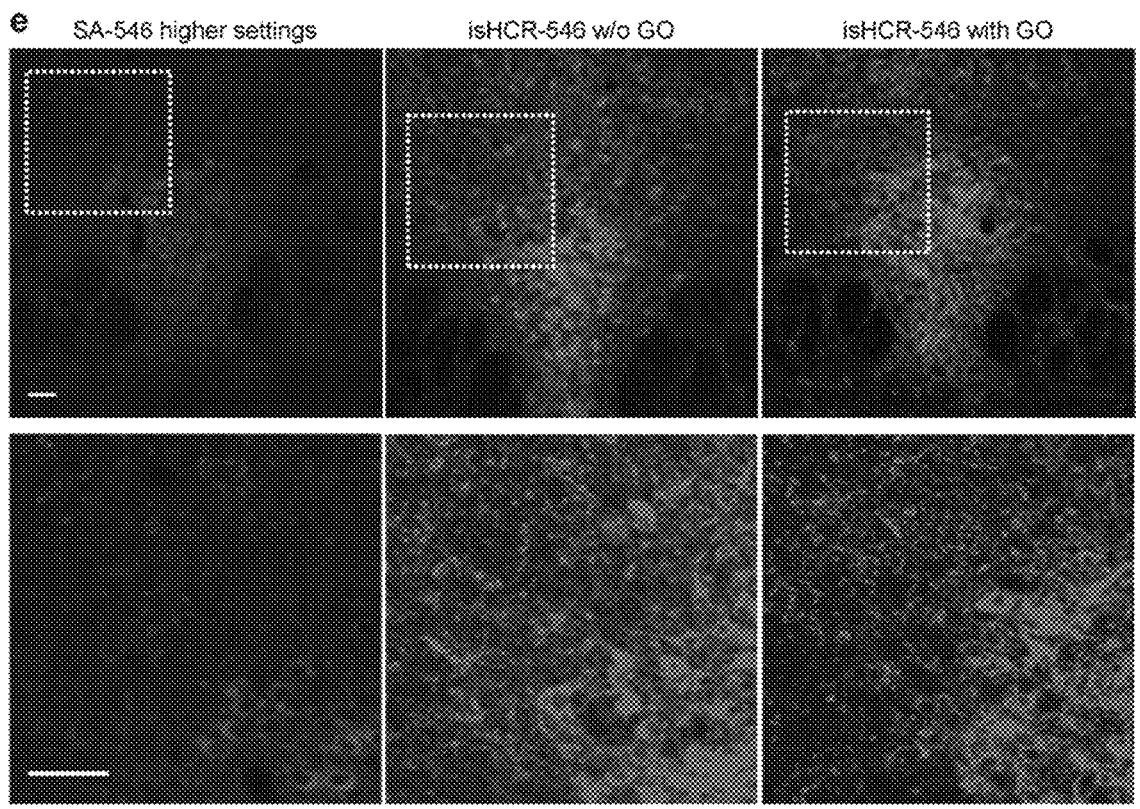
Figure 7A:
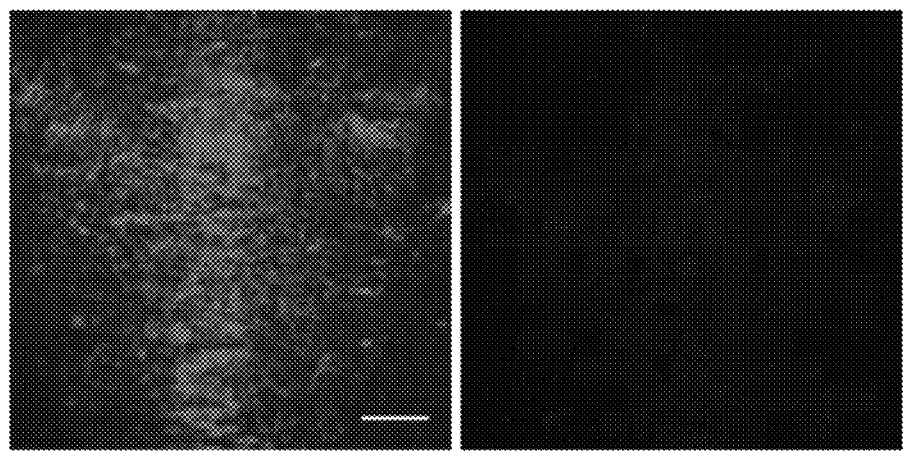
FIG. 7. isHCR specifically amplifies Vglut3 immunosignals in mouse brain sections.
Figure 7B:
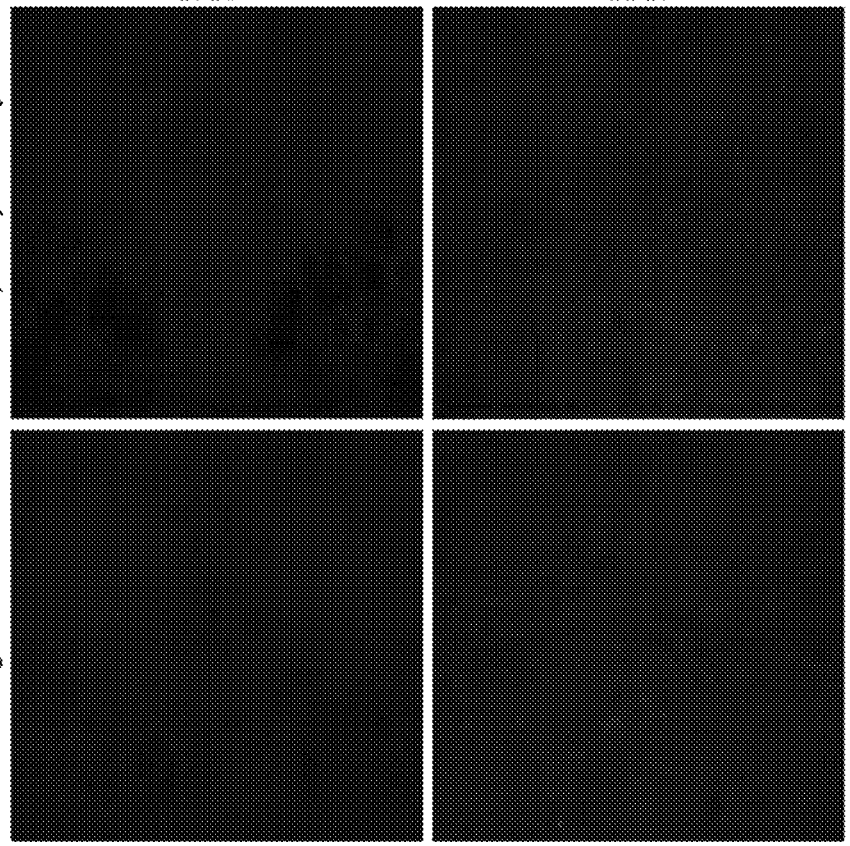
Figure 7C:
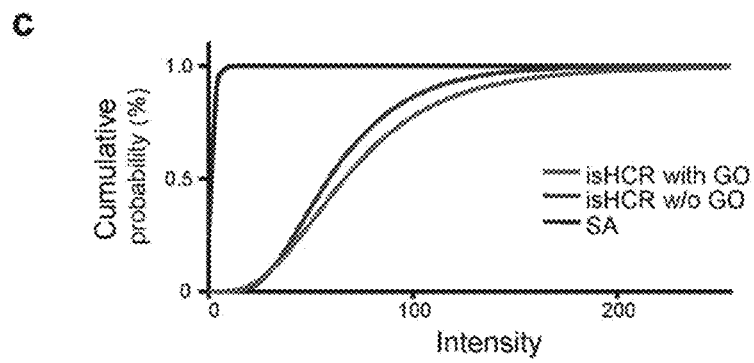
Figure 7D:
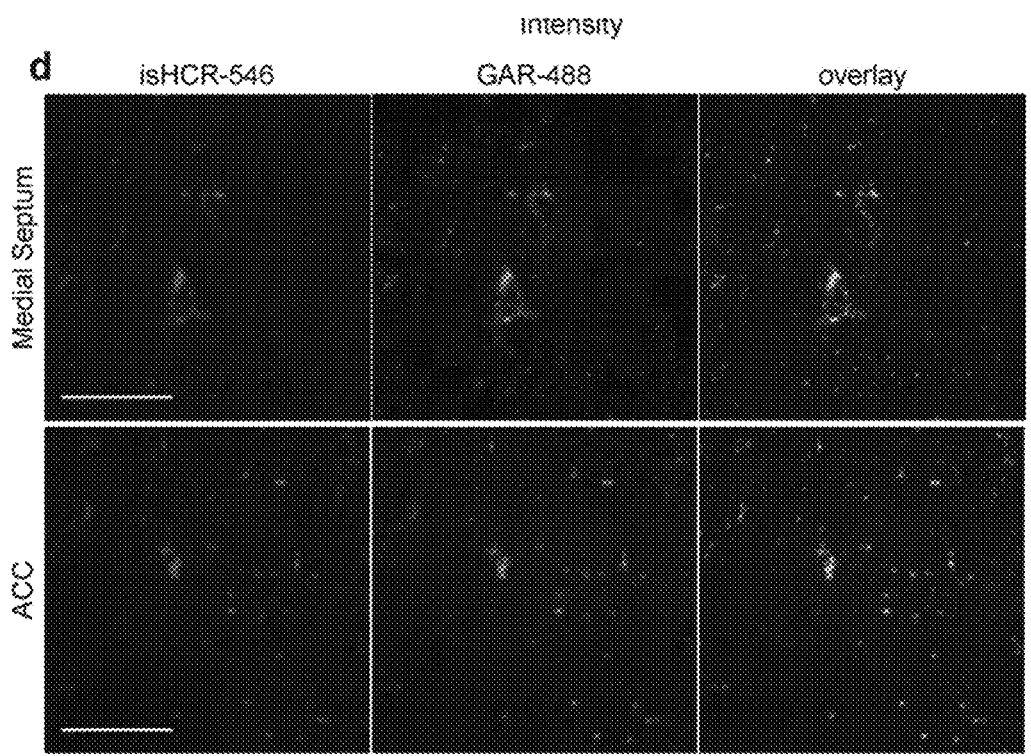
Figure 8A:
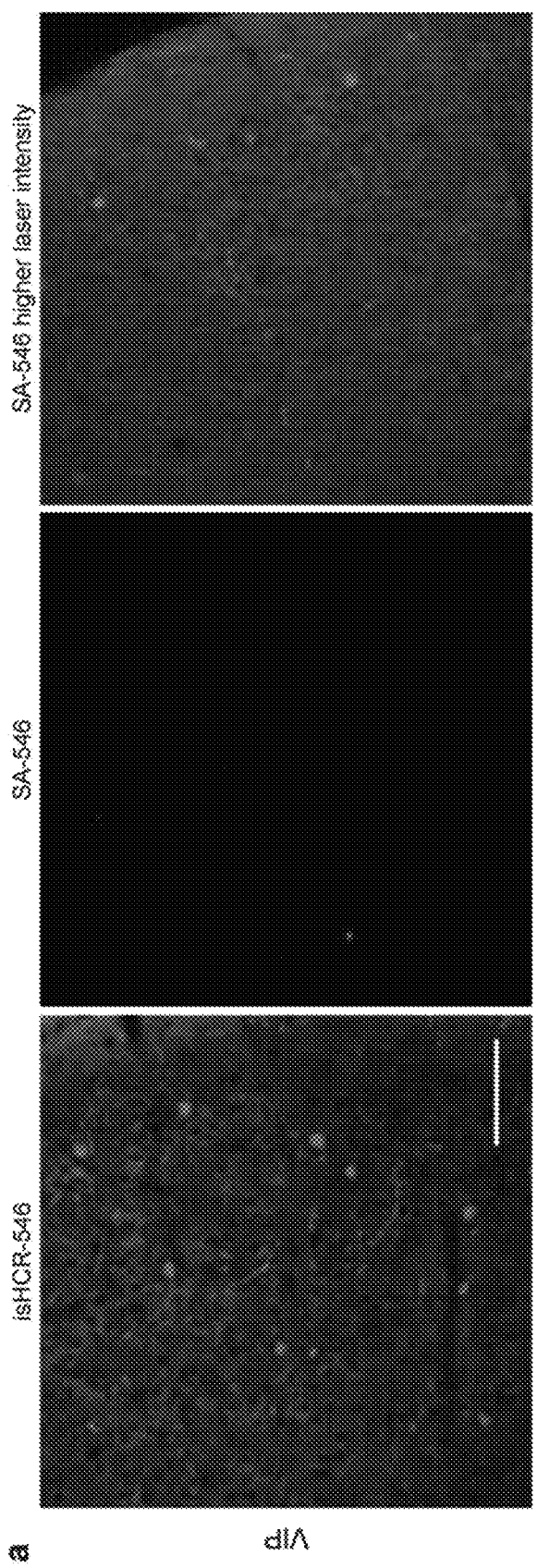
FIG. 8. isHCR effectively amplifies various immunofluorescence signals.
Figure 8B:
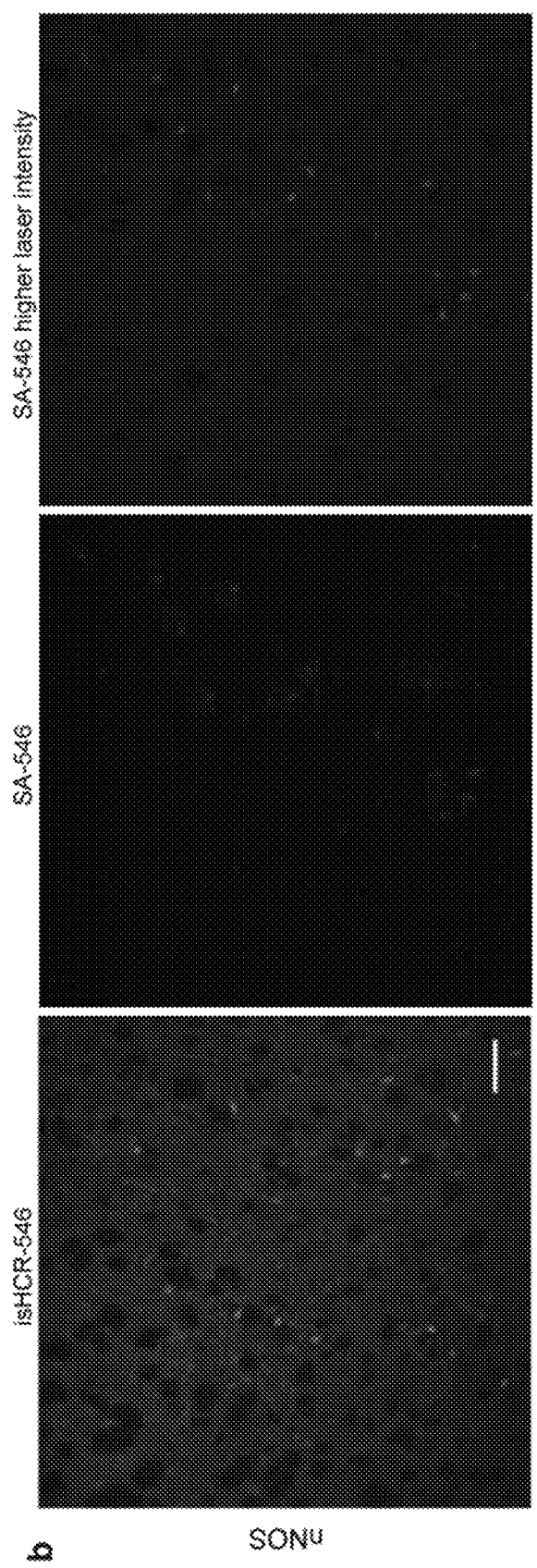
Figure 8C:
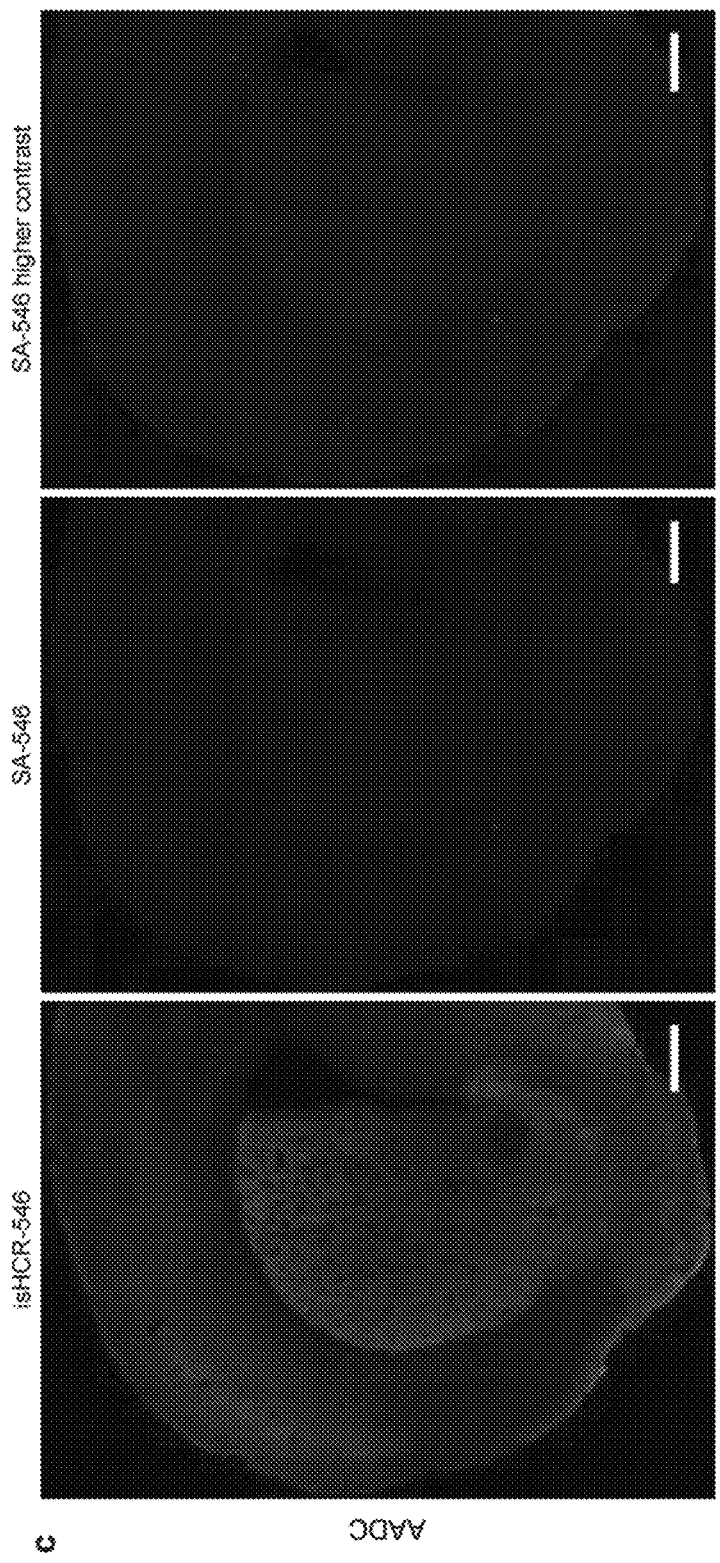

In the seventh embodiment, immunostainings against a membrane protein, a peptide neurotransmitter, and two enzymes were carried out to examine the generality of isHCR with GO in brain sections. It has been challenging to localize the expression of vesicular glutamate transporter-3 (Vglut3; a vesicular membrane protein) using standard IHC method (FIG. 5e and FIG. 7a). isHCR conducted without the addition of GO produced strong labeling signals in the brainstem raphe nuclei but also showed high background noise. Encouragingly, isHCR with the addition of GO reduced the background and revealed sharp, punctate labeling of Vglut3-positive synaptic terminals (FIG. 5e and FIG. 7a, c). No specific labeling was observed in brain sections without primary antibody or in mutant mice lacking the functional gene encoding Vglut3 (FIG. 7b). Additional control experiments verified that isHCR faithfully amplified the true Vglut3 signals and preserved spatial resolution for confocal imaging (FIG. 7d, e). The inventors next used isHCR to examine the expression patterns of vasoactive intestinal peptide (VIP), neuronal nitric oxide synthase (nNOS), and aromatic L-amino acid decarboxylase (AADC) in brain sections. In all cases, isHCR with GO produced strong immunopositive signals with low background, consistently revealing much richer expression patterns for each of these proteins than were observed with traditional IHC method (FIG. 8).

Figure 9A:
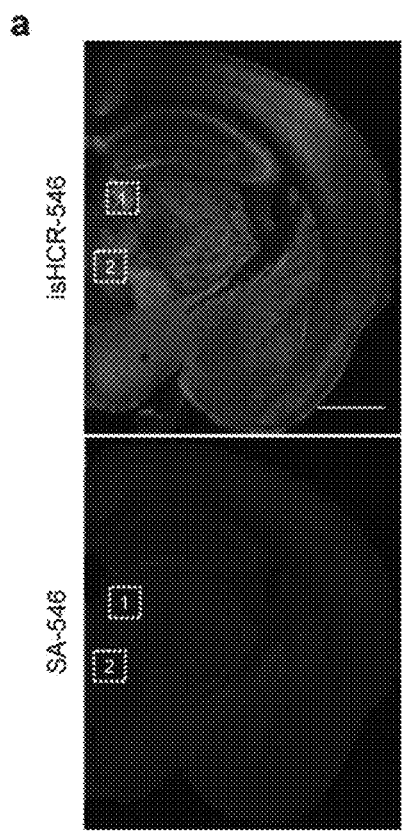
FIG. 9. isHCR enables the detection of biomolecules that are challenging for a standard IHC method.
Figure 10A:
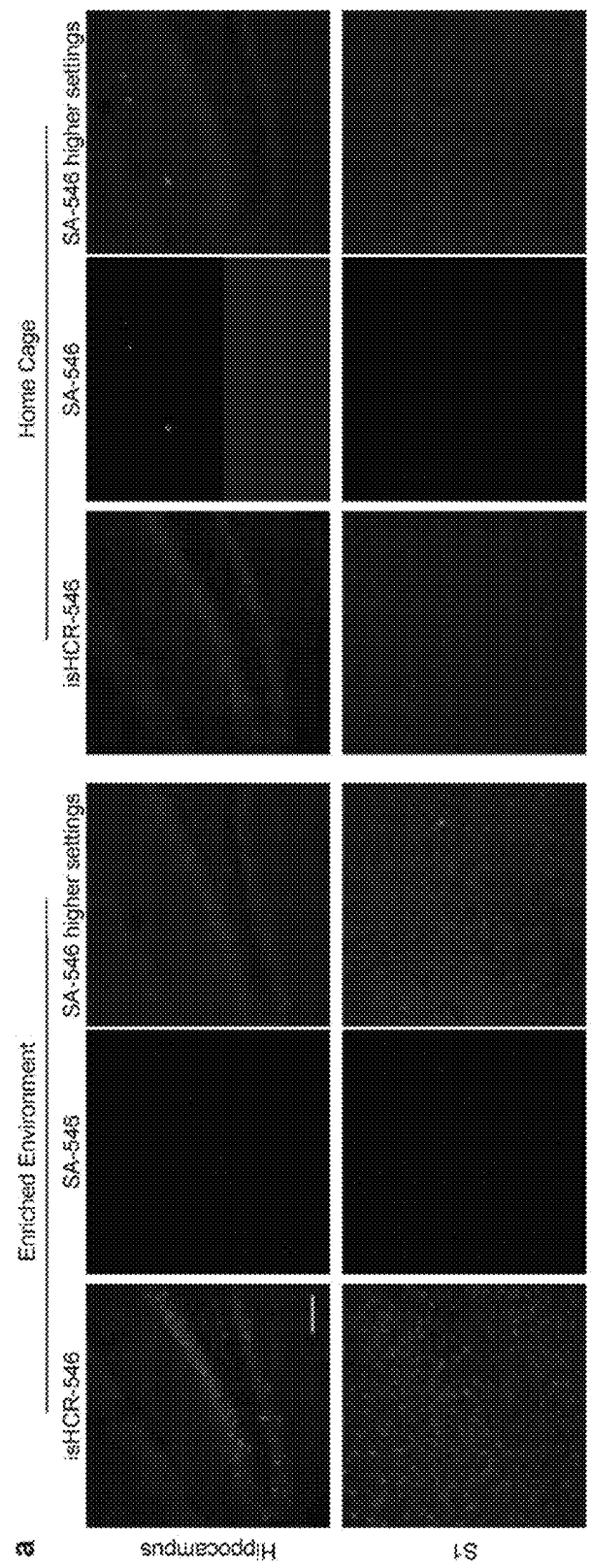
FIG. 10. isHCR amplification enables the detection of low-abundance proteins.

Our successful use of GO to decrease background signal intensity prompted us to explore the use of isHCR with monoclonal antibodies. Although monoclonal antibodies are often more specific than polyclonal antibodies, they frequently fail to provide a sufficiently strong signal for detection via traditional IHC staining. In the sixth embodiment, the inventors used two strategies to test isHCR with monoclonal antibodies in mouse brain sections: a biotinylated primary monoclonal antibody against GAD67, and the combination of a primary monoclonal antibody against c-Fos with a biotinylated secondary antibody (FIG. 9a, b and FIG. 10a). In both cases, much stronger signals in the isHCR-amplified samples than in the non-isHCR samples were obtained.

Figure 9B:
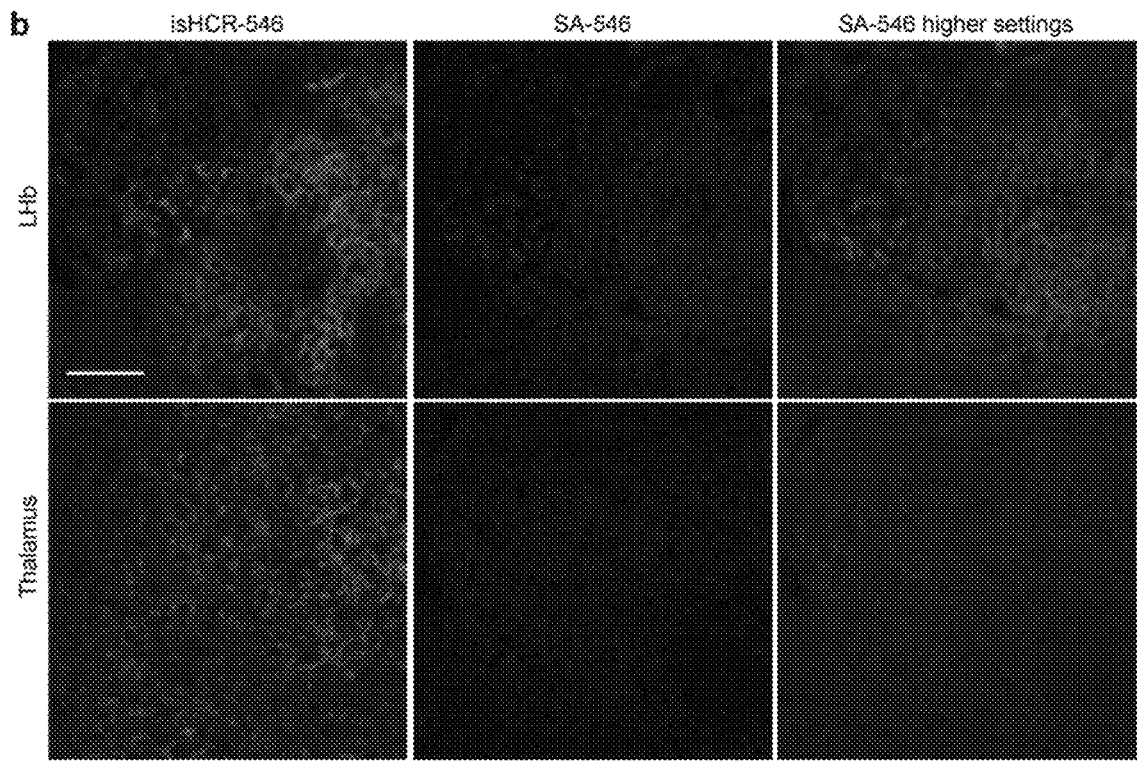
Figure 9C:
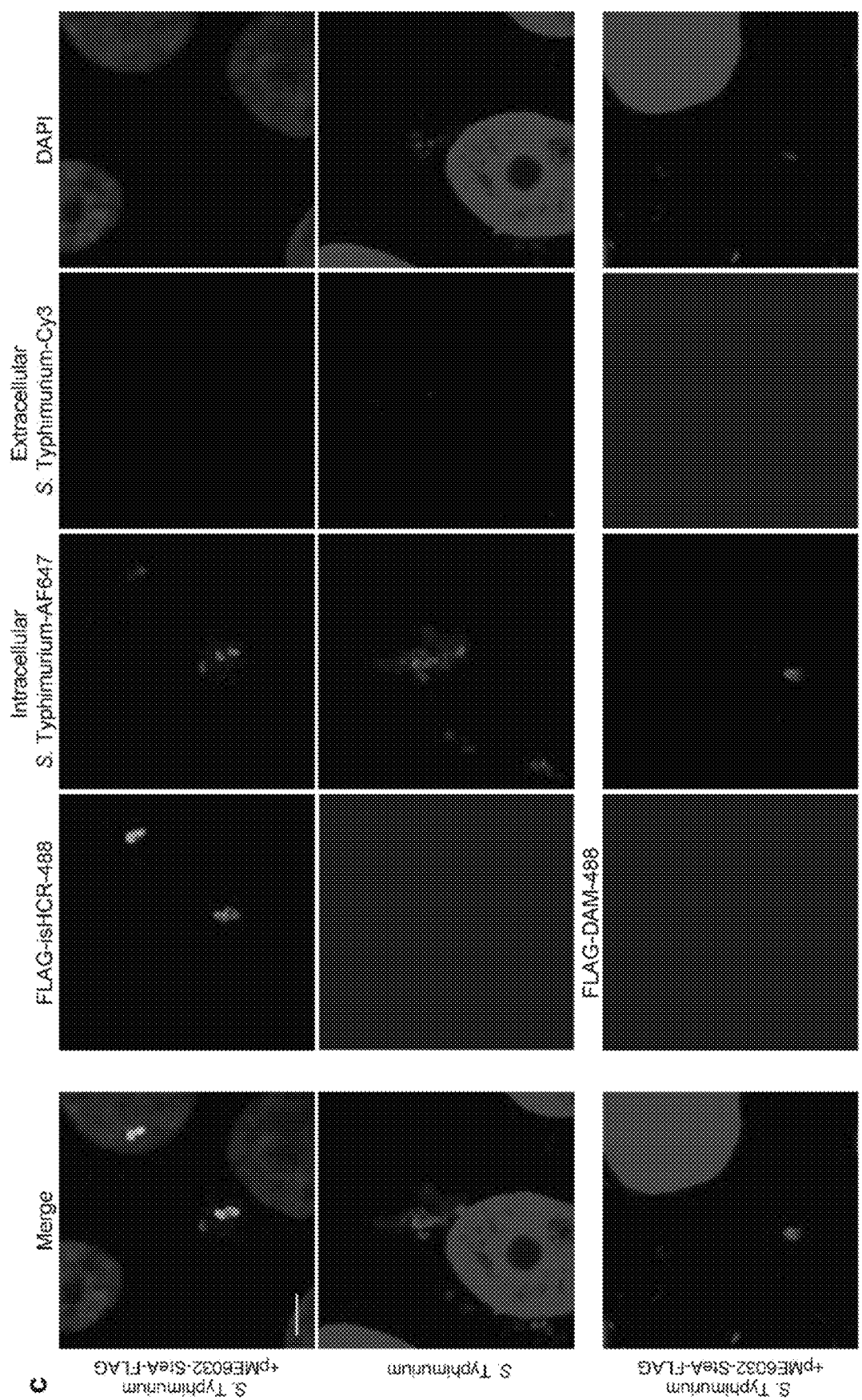
Figure 10B:
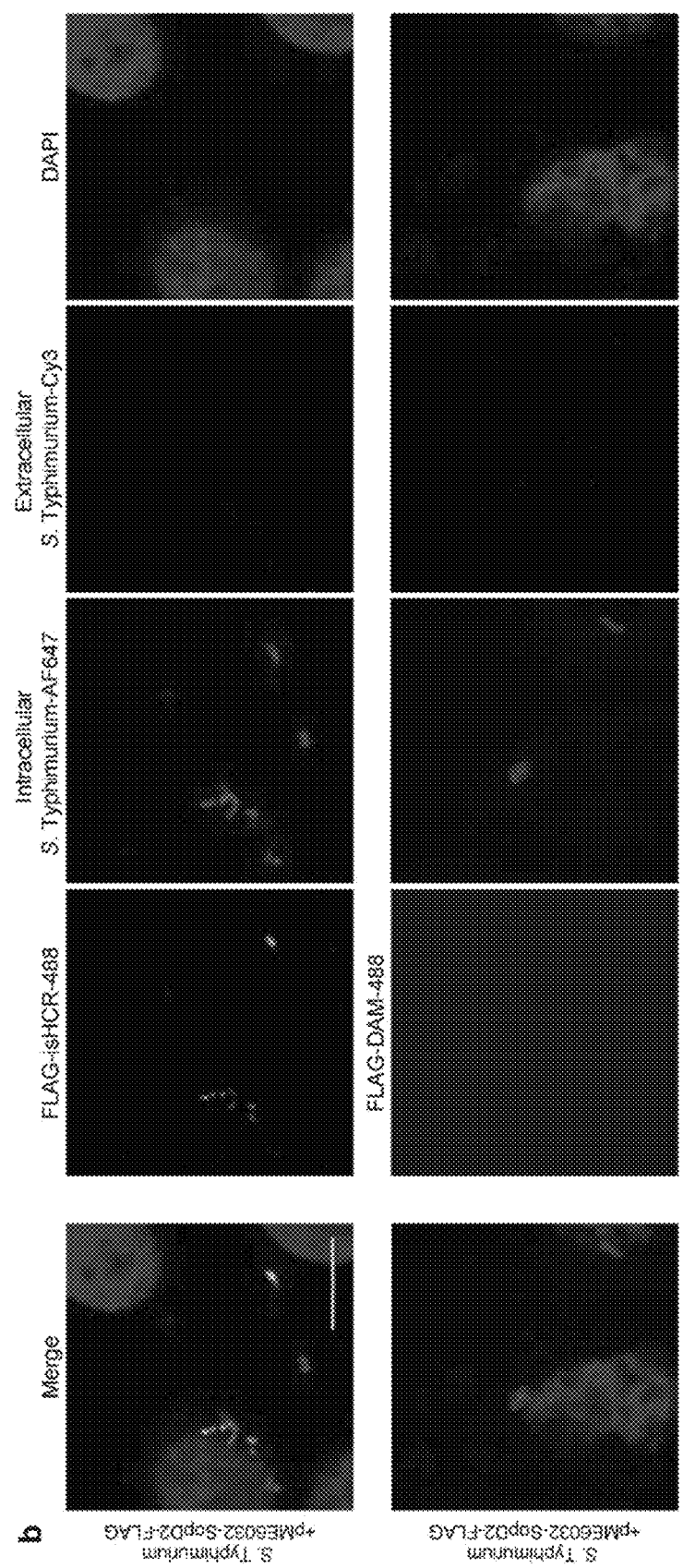

More importantly, isHCR using GO enabled detection of immunosignals that were too weak for traditional IHC. Bacterial pathogens deliver protein effectors into host cells to manipulate their physiology; however, the presence and precise distribution of some translocated effectors remain unclear because their concentrations are extremely low. In the seventh embodiment, the inventors tagged the *Salmonella enterica* serovar *Typhimurium* (*S. Typhimurium*) effectors SteA and SopD2 with FLAG-tags and expressed these fusion proteins in *S. Typhimurium*, and used these transformed strains to infect HeLa cells. (FIG. 9c and FIG. 10b). isHCR amplification yielded strong signals in cells infected with *S. Typhimurium* expressing the FLAG-tagged SteA and SopD2 proteins, but not in uninfected HeLa cells or in HeLa cells infected with wild-type *S. Typhimurium* (FIG. 9c top and middle panels; FIG. 10b, c). In contrast, a standard IHC staining method failed to detect any FLAG-tag epitope signal (FIG. 9c lower panel and FIG. 10b). These results thus highlight the utility of isHCR amplification for making new biological discoveries.

HCR is the abbreviation of Hybridization Chain Reaction. When a single-stranded DNA initiator is added to a reaction system, it opens a hairpin of one species (H1 amplifier), exposing a new single-stranded region that opens a hairpin of the other species (H2 amplifier). This process, in turn, exposes a single-stranded region identical to the original initiator. The resulting chain reaction leads to the formation of a nicked double helix that grows until the hairpin supply is exhausted.

Click chemistry is a class of biocompatible reactions intended primarily to join substrates of choice with specific biomolecules. Click chemistry is not a single specific reaction, but describes a way of generating products that follow examples in nature, which also generates substances by joining small modular units. In general, click reactions usually join a biomolecule and a reporter molecule. Click chemistry is not limited to biological conditions: the concept of a "click" reaction has been used in pharmacological and various biomimetic applications. However, they have been made notably useful in the detection, localization and qualification of biomolecules. The typical click chemistry reaction includes (1) cycloadditions, such as the Huisgen 1,3-dipolar cycloaddition, in particular the Cu(I)-catalyzed stepwise variant; (2) thiol-ene reaction; (3) diels-Alder reaction and inverse electron demand Diels-Alder reaction; (4) cycloadditions between isonitriles (isocyanides) and tetrazines; (5) nucleophilic substitution especially to small strained rings like epoxy and aziridine compounds; (6) carbonyl-chemistry-like formation of ureas but not reactions of the aldol type due to low thermodynamic driving force; and (7) addition reactions to carbon-carbon double bonds like dihydroxylation or the alkynes in the thiol-yne reaction.

Graphite oxide is a compound of carbon, oxygen, and hydrogen in variable ratios, obtained by treating graphite with strong oxidizers. The maximally oxidized bulk product is a yellow solid with C:O ratio between 1.3 and 2.9, that retains the layer structure of graphite but with a much larger and irregular spacing.

Antibody in the present invention includes but not limit to traditional IgGs and nanobodies.

EXAMPLES

Methods and Materials

Reagents and reagent preparation. DNA oligos were synthesized by Thermo Fisher Scientific and Sangon Biotech. Detailed sequences and modifications of DNA oligos can be found in Table 1. All oligos were dissolved in ddH$_2$O and stored at −20° C.

The detailed information for antibodies and fluorescent reagents is shown in Table 2. Dextran sulfate (D8906) were purchased from Sigma-Aldrich. Graphene Oxide (GO, XF020, particle size <500 nm, C/O ratio=1.6) was obtained from Nanjing XFNANO Materials Tech Co., Ltd.

Plasmid construction. scFv-GCN4-HA-GB1 sequence was amplified from pHR-scFv-GCN4-sfGFP-GB1-NLS-dWPRE (Addgene plasmid #60906, a gift from Ron Vale). For membrane targeting, a GAP43-palmitoylation sequence was added by PCR to the 5' end of GFP (hereafter named mGFP). mGFP was cloned into the pcDNA3.1 vector. scFv-GCN4-HA-GB1 was cloned into the pET-21a vector for bacterial cytosolic expression. The sequences encoding *S. Typhimurium* effectors SteA or SopD2 were amplified by PCR from genomic DNA of a wild-type *S. Typhimurium* strain SL1344. SteA and SopD2 were then cloned into pME6032 with a C-terminal FLAG-tag.

Purification of recombinant protein. *E. coli* BL21 (DE3) cells harboring pET-21a-scFv-GCN4-HA-GB1 were grown in lysogeny broth (LB) medium supplemented with 100 μg mL$^{-1}$ ampicillin. Protein expression was induced with IPTG at a concentration of 0.1 M for 3 h at 37° C.

Cells were then pelleted by a 20-min spin at 2,000×g at 4° C. Cells were lysed via ultrasonic sonication. Cellular debris was removed via 1 h of centrifugation at 39,000×g at 4° C. The supernatant was bound to His-Select nickel affinity resin, washed with His-wash buffer (20 mM NaH$_2$PO$_4$, pH 8.0, 1 M NaCl, 20 mM imidazole), eluted with His-elution buffer (20 mM sodium phosphate, pH 8.0, 0.5 M NaCl, 250 mM imidazole), and the eluate was then dialyzed with phosphate buffer saline (PBS).

Protein-HCR DNA Initiator conjugation. The conjugation was performed using Maleimide-PEG2-NHS (SMCC, 746223, Sigma-Aldrich) or NHS-Azide (synthesized or purchased from Thermo Fisher Scientific, 26130) as linkers. For Maleimide-PEG2-NHS conjugation, proteins (IgGs) were dialyzed into phosphate buffered saline (PBS, pH 7.4) and reacted with Maleimide-PEG2-NHS (7.5-fold molar excess) at room temperature for 2 h. Excess crosslinkers were removed from maleimide-activated proteins using Zeba spin columns (7000 MWCO). In parallel, thiol-modified HCR initiators were reduced using dithiothreitol (DTT, 100 mM) in PBS (1 mM EDTA, pH 8.0) for 2 h at room temperature, and then purified using Micro Bio-Spin P-6 Gel columns. The maleimide-activated proteins and reduced initiators (15-fold molar excess for IgGs) were mixed and reacted at room temperature for 2 h. HCR initiator-labeled proteins were purified using Amicon Ultra Centrifugal Filters (50 kDa MWCO) or Zeba spin columns (7000 MWCO).

For NHS-Azide conjugation, proteins were dialyzed into phosphate buffered saline (PBS, pH 7.4) and reacted with NHS-Azide (7.5-fold molar excess) at room temperature for 2 h. Excess crosslinkers were removed from azide-activated proteins using Zeba spin columns (7000 MWCO). The azide-activated proteins were mixed with DBCO-labeled HCR initiators (15-fold molar excess for IgGs) and then reacted at room temperature for 12 h. HCR initiator-labeled proteins were purified using Amicon Ultra Centrifugal Filters (50 kDa MWCO) or Zeba spin columns (7000 MWCO).

Cell culture and bacterial infections. HEK293T cells (ATCC CRL-3216) and HeLa cells (ATCC CCL-2) were used for the cultured-cell staining experiments. Cells were seeded on 12 mm #1.5 coverglass slips. Transfection was done using PEI. Cells were fixed with paraformaldehyde before subsequent experiments. The *S. Typhimurium* infection was performed according to a previous report (Shi, J. et al. *Nature* 514, 187-192 (2014)).

Mice. Animal care and use were in accordance with the institutional guidelines of the National Institute of Biological Sciences, Beijing (NIBS), as well as the governmental regulations of China.

Adult (8-12 weeks old) Vglut3−/− mice (Liu, Z. et al. *Neuron* 81, 1360-1374 (2014)) and C57BL/6N mice of either sex were used. Mice were maintained with a 12/12 photoperiod (light on at 8 AM) and were provided food and water ad libitum. Mice were anaesthetized with pentobarbital (i.p., 80 mg×kg$^{-1}$) before scarification.

Mouse behaviors. The enriched environment experiments were performed using adult (8-12 weeks old) C57BL/6N male mice according to the following protocol. The mice were singly housed three days before the experiments. They were randomly assigned into the "environmentally enriched" group and "homecage control group" (n=3 mice for each group). The enriched environment arena was a 50×50 cm plastic box containing a running wheel, a plastic tunnel, wooden chips for chewing, and buried food. The mice from experimental groups (n=3 mice) were allowed to explore the arena for 1 h. The mice were removed from the novel environment and returned to the homecage. The mice were sacrificed after 30 min. Homecage control mice (n=3 mice) were sacrificed directly without exploring the arena. c-Fos expression was examined without blinding.

Tissue sample preparation. Mice were anesthetized with an overdose of pentobarbital and perfused intracardially with PBS, followed by paraformaldehyde (PFA, 4% wt/vol in PBS). Tissues (brains or lungs) were dissected out and postfixed in 4% PFA for 4 h at room temperature or 1 d at 4° C. Tissue samples were first dehydrated in 30% sucrose solution for preparing thin sections (50 μm). The thickness of mouse brain sections was 50 μm for immunofluorescent labeling. Thin sections were prepared on a Cryostat microtome (Leica CM1950). The brain section samples for those experiments that compared the signal intensity from isHCR amplification and traditional IHC methods were serial sections from the same mice, and were prepared on the same day. Serial sections were divided equally into two groups for the subsequent experiments.

Immunohistochemistry. The detailed information, working concentrations, and incubation times for antibodies can be found in Table 2. For brain sections and cultured cells, samples were permeabilized with 0.3% Triton X-100 in PBS (PBST) and blocked in 2% BSA in PBST at room temperature for 1 h. Sections were then incubated with primary antibodies. Samples were washed three times in PBST and were then incubated with biotinylated or HCR initiator-conjugated secondary antibodies. For control experiments, we used a mixture containing equal amounts of fluorophore-conjugated secondary antibodies and biotinylated secondary antibodies. Samples were then washed again three times in PB ST. The biotinylated secondary antibodies were visualized by fluorophore-conjugated Streptavidin or DNA-fluorophore HCR amplifiers. HCR initiator-conjugated secondary antibodies were visualized by DNA-fluorophore HCR amplifiers.

For *S. Typhimurium* infected HeLa cells, samples were washed with PBS once, and fixed using 4% PFA for 15 min at room temperature. Samples were washed three times in PBS to remove PFA, and were then incubated with anti-Salmonella primary antibody at room temperature for 1 h. Samples were then washed again three times in PBS. Cy3-conjugated goat anti-rabbit secondary antibodies were applied to detect extracellular *S. Typhimurium*. After incubation at room temperature for 1 h, samples were washed three times in PBS. Samples were then permeabilized in 0.3% PBST for 5 min at room temperature. Samples were incubated in an antibody mixture containing anti-FLAG and anti-*Salmonella* primary antibodies for 1 h at room temperature. Samples were washed three times in PBS to remove the unbound primary antibodies. A mixture containing biotinylated donkey anti-mouse secondary antibody (for detecting FLAG-tag) and Alexa Fluor-647 conjugated secondary antibody (for detecting intracellular *S. Typhimurium*) was applied. Samples were washed three times in PBS after incubation at room temperature for 1 h. The biotinylated donkey anti-mouse secondary antibodies were visualized by fluorophore-conjugated streptavidin or DNA-fluorophore HCR amplifiers.

Labeling of isHCR initiators. All reagents were dissolved in HCR amplification buffer [5× sodium chloride citrate (SCC buffer), 0.1% vol/vol Tween-20, and 10% wt/vol dextran sulfate in ddH$_2$O]. After labeling with biotinylated secondary antibodies, samples were incubated in 1 μg·mL$^{-1}$ streptavidin at room temperature for 30 min. After being washed three times in PBST, samples were incubated with 0.5 μM DNA-biotin HCR initiators at room temperature for 30 min. Samples were then washed three times and stored in PBST.

isHCR amplification. Note that while the experimental steps regarding the isHCR initiators varied according the conjugation strategies, the basic isHCR amplification process is common to all of the experiments. First, HCR amplification buffer was prepared [5× sodium chloride citrate (SCC buffer), 0.1% vol/vol Tween-20, and 10% wt/vol dextran sulfate in ddH2O]. Next, a pair of DNA-fluorophore HCR amplifiers were snap-cooled separately in 5× SSC buffer by heating at 95° C. for 90 s and cooling to room temperature over 30 min. Both of these amplifiers were then added to amplification buffer (typically to a final concentration of 12.5 nM for thin sections). isHCR amplification proceeded as samples were incubated with this buffer overnight at room temperature, and free amplifiers were then removed by washing the three times with PBST prior to signal detection. Note that an additional graphene oxide step was added to this basic process for applications that demands background suppression. Briefly, to include the quenching step, GO (20 μg·mL$^{-1}$) was mixed with the amplifiers in amplification buffer. The amplifier/GO mixture was vortexed thoroughly and incubated at room temperature for at least 5 min before being added to initiator-labeled samples.

To perform multi-round amplification, we used DNA-biotin HCR amplifiers. Before use, DNA-biotin HCR amplifiers were snap-cooled. Samples were incubated with 12.5 nM DNA-biotin HCR amplifiers overnight at room temperature. After extensive washing, streptavidin (1 μg·mL$^{-1}$) was applied again to start the next round of amplification. The procedure of adding DNA-biotin HCR amplifiers and then streptavidin was repeated two or three times to achieve desired signal intensity. DNA-fluorophore amplifiers (12.5 nM) were used in the final round to visualize the signals. For control experiments, biotin and Alexa Fluor-488 dual-labeled HCR amplifiers were used for the first round of amplification. Alexa Fluor-546-labeled HCR amplifiers were used for the second round of amplification.

We initially conducted tests of the effects of GO on the performance of both unassembled and polymerized HCR amplifiers (FIG. 5c). Here, DNA-Alexa Fluor 546 HCR amplifiers were snap-cooled and added to the amplification buffer at the final concentrations of 12.5 nM, and GO (20 μg·mL$^{-1}$) was added to quench the fluorescence of free HCR amplifiers in solution. After 5 min of quenching, DNA-biotin HCR initiators (0.5 μM) were added to trigger the polymerization of HCR amplifiers and the attendant recovery of fluorescence. After incubating samples overnight at room temperature, we measured the fluorescence of samples using a Molecular Device SpectraMax M3 microplate reader.

Fluorescence microscopy. Confocal microscopy was performed on a Zeiss Meta LSM510 confocal scanning microscope using a 10×0.3 NA, a 20×0.5 NA, a 63×1.4 NA, or a 100×1.3 NA objective, or on a Zeiss LSM880 confocal scanning microscope using a 20×0.5 NA or a 40×0.75 NA objective. Images were processed and measured with FIJI and Matlab. For confocal imaging, brain sections from both groups were imaged using identical laser intensity, pin hole value, detector gain, and offset. In some experiments, higher laser intensities were used to image brain sections for the SA group samples: such images have been labeled as 'higher laser intensity' in the figures.

To image the entire brain sections, we performed widefield fluoresce imaging using the Olympus VS120 virtual microscopy slide scanning system with a 10× objective. For slide scanner imaging, brain sections from both groups on the same slide were imaged during the same imaging run using identical light intensity and exposure time. The images were acquired at 16 bit and were converted directly to the TIFF format for publication.

Figure 7E:
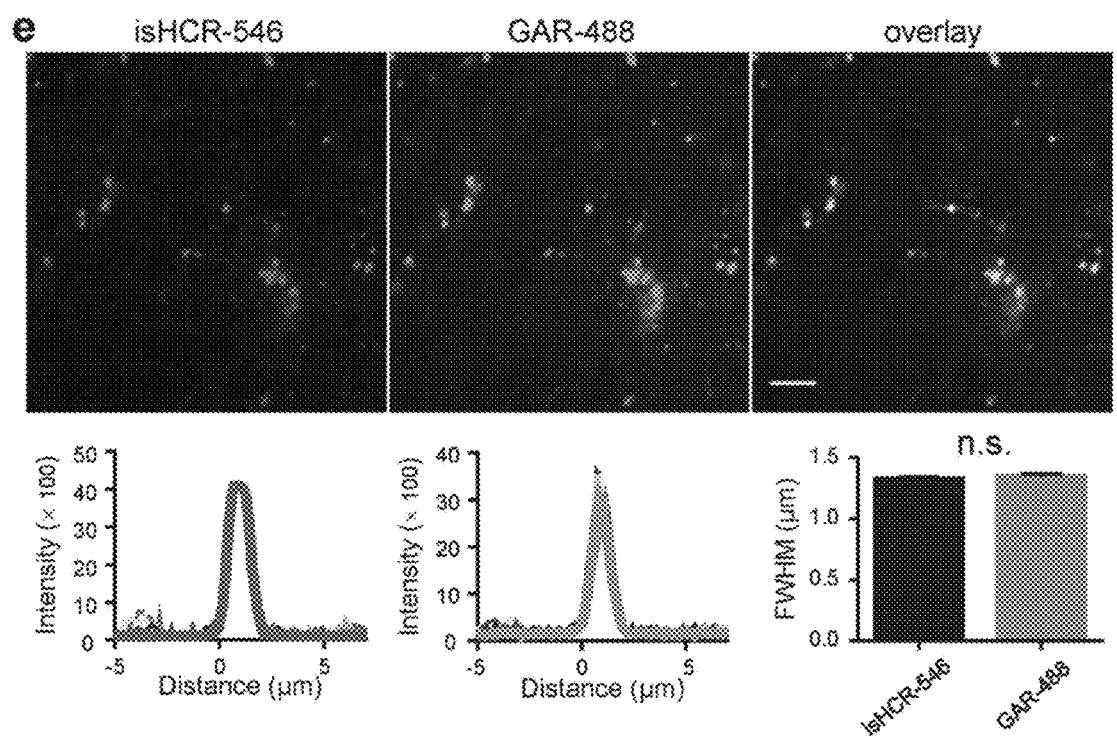

Data analysis. To determine the width of immunopositive neuronal processes or cell membrane (FIG. 1e, FIGS. 3b, and 7e), we calculated the full width at half maximum (FWHM) using signals from either unamplified or isHCR-amplified channels (Ramanathan, S. P. et al. *Nat. Cell Biol.* 17, 148-159 (2015)). A series of straight lines perpendicular to the membrane or neuronal process were drawn (FIG. 1e and FIG. 3a). The corresponding intensity profiles were plotted and averaged for each channel. For neuronal process measurement, the baseline correction was applied. The corrected average intensity of each channel was fit to a Gaussian distribution with a non-linear least square method. FWHM was calculated with the equation: FWHM=$2\sqrt{2\ln 2}\sigma$, where σ is the standard deviation of the fitted Gaussian curve. For cell membrane measurement, the mean intensity of the distance from the edge of the membrane or neuronal process (typically between −3 μm to −2 μm) was calculated as the baseline (denoted m). The peak value of the curve was determined (denoted p). Half-peak intensity (I) was defined (p+m)/2. The full width at half maximum (FWHM) was quantified as the width of the average intensity curve at I.

To determine the dynamic range of blotting signals (FIG. 2), the peak intensity area of each lane was calculated and plotted using the signals acquired with short or long exposure time. We then plotted the intensity values vs. analyte protein amount using a $\log_2$ scale. We then performed a series of linear regression across ranges of protein amount and calculated the R-squared value for each regression. The linear dynamic range represented the range that reported the maximum R-squared value.

To calculate the amplification factors of isHCR in brain sections (FIG. 6), we performed NeuN immunostaining using anti-NeuN primary antibodies with different dilution ratios. We then visualized the signals using isHCR (with or without GO) or SA-546. The images of isHCR-546 and SA-546 samples from the ACC, DS, and MS were acquired using identical microscopy settings. We then calculated the average signal intensity within each data group.

Statistical significance was determined using t-test or Kolmogorov-Smirnov test. $P<0.05$ was considered significant.

TABLE 1

| Oligo nucleotide sequences and modifications | | |
|---|---|---|
| Name | Sequence (5' to 3') | Modifications |
| B1 I2 | ATATAgCATTCTTTCTTgAggAgggCAg CAAACgggAAgAg(SEQ ID NO: 1) | 5' Biotin |
| B1 I2 Thiol | ATATAgCATTCTTTCTTgAggAgggCAg CAAACgggAAgAg(SEQ ID NO: 1) | 5' Thiol |
| B1 I2 DBCO | ATATAgCATTCTTTCTTgAggAgggCAg CAAACgggAAgAg(SEQ ID NO: 1) | 5' DBCO |

TABLE 1 -continued

Oligo nucleotide sequences and modifications

| Name | Sequence (5' to 3') | Modifications |
| --- | --- | --- |
| B1 Amplifier H1 546 | CgTAAAggAAgACTCTTCCCgTTTgCTg CCCTCCTCgCATTCTTTCTTgAggAggg CAgCAAACgggAAgAg(SEQ ID NO: 2) | 5' Alexa Fluor 546 |
| B1 Amplifier H2 546 | gAggAgggCAgCAAACgggAAgAgTCTT CCTTTACgCTCTTCCCgTTTgCTgCCCT CCTCAAgAAAgAATgC(SEQ ID NO: 3) | 3' Alexa Fluor 546 |
| B1 Amplifier H1 Terminal Biotin | CgTAAAggAAgACTCTTCCCgTTTgCTg CCCTCCTCgCATTCTTTCTTgAggAggg CAgCAAACgggAAgAg(SEQ ID NO: 2) | 5' Biotin |
| B1 Amplifier H2 Terminal Biotin | gAggAgggCAgCAAACgggAAgAgTCTT CCTTTACgCTCTTCCCgTTTgCTgCCCT CCTCAAgAAAgAATgC(SEQ ID NO: 3) | 3' Biotin |
| B1 Amplifier H1 Internal Biotin | CgTAAAggAAgACTCTTCCCgTTTgCTg gCCCTCCTCgCATTCTTTCTTAggAggg CAgCAAACgggAAgAg(SEQ ID NO: 2) | Internal Biotin |
| B1 Amplifier H2 Internal Biotin | gAggAgggCAgCAAACgggAAgAgTCTT CCTTTACgCTCTTCCCgTTTgCTgCCCT CCTCAAgAAAgAATgC(SEQ ID NO: 3) | Internal Biotin |
| B1 Amplifier H1 Internal Biotin and 5'-488 | CgTAAAggAAgACTCTTCCCgTTTgCTg CCCTCCTCgCATTCTTTCTTgAggAggg CAgCAAACgggAAgAg(SEQ ID NO: 2) | Internal Biotin 5' Alexa Fluor 488 |
| B1 Amplifier H2 Internal Biotin and 3'-488 | gAggAgggCAgCAAACgggAAgAgTCTT CCTTTACgCTCTTCCCgTTTgCTgCCCT CCTCAAgAAAgAATgC(SEQ ID NO: 3) | Internal Biotin 3' Alexa Fluor 488 |
| B5 I2 | ATATACACTTCATATCACTCACTCCCAA TCTCTATCTACCC(SEQ ID NO: 4) | 5' Biotin |
| B5 I2 Thiol | ATATACACTTCATATCACTCACTCCCAA TCTCTATCTACCC(SEQ ID NO: 4) | 5' Thiol |
| B5 I2 DBCO | ATATACACTTCATATCACTCACTCCCAA TCTCTATCTACCC(SEQ ID NO: 4) | 5' DBCO |
| B5 Amplifier H1 488 | ATTggATTTgTAgggTAgATAgAgATTg ggAgTgAgCACTTCATATCACTCACTCC CAATCTCTATCTACCC(SEQ ID NO: 5) | 5' Alexa Fluor 488 |
| B5 Amplifier H2 488 | CTCACTCCCAATCTCTATCTACCCTACA AATCCAATgggTAgATAgAgATTgggAg TgAgTgATATgAAgTg(SEQ ID NO: 6) | 3' Alexa Fluor 488 |

TABLE 2

Antibodies and Fluorescent reagents

Primary antibodies:

| Epitope | Vendor | Cat. No. | Dilution | Incubation Time |
| --- | --- | --- | --- | --- |
| GFP | Thermo Fisher Scientific | A10259 | 1:1000 | Overnight at 4° C. for brain sections; 1 h at RT for cultured cells and western blotting |
| Vglut3 | Synaptic Systems | 135 203 | 1:1000 | 48 h at 4° C. for brain sections |
| Tyrosine Hydroxylase (TH) | Millipore | ab152 | 1:1000 | Overnight at 4° C. for brain sections |
| Choline acetyltransferase (ChAT) | Millipore | AB144P | 1:500 | Overnight at 4° C. for brain sections |
| Vasoactive intestinal peptide (VIP) | ImmunoStar | 20077 | 1:500 | Overnight at 4° C. for brain sections |

TABLE 2-continued

| Antibodies and Fluorescent reagents | | | | |
|---|---|---|---|---|
| DOPA decarboxylase (AADC) | Abcam | ab3905 | 1:500 | 24 h at 4° C. for brain sections |
| Neuronal nitric oxide synthase (nNOS) | Sigma | N7280 | 1:500 | Overnight at 4° C. for brain sections |
| GAD67 | Millipore | MAB5406B | 1:1000 | Overnight at 4° C. for brain sections |
| NeuN | Millipore | ABN78 | 1:1000-1:50000 | Overnight at 4° C. for brain sections |
| c-Fos | Santa Cruz | sc-166940 | 1:200 | 48 h at 4° C. for brain sections |
| FLAG | Sigma | F1804 | 1:1000 | 1 h at RT for cultured cells |
| Salmonella | Abcam | ab35156 | 1:1000 | 1 h at RT for cultured cells |
| HA | BioLegend | 901505 | 1:500 | 1 h at RT for Western blot |
| Substance P | Abcam | ab7340 | 1:200 | 48 h at 4° C. for brain sections |

| Secondary antibodies: | | | | | |
|---|---|---|---|---|---|
| Secondary ab. | Vendor | Label | Cat. No. | Dilution | Incubation Time |
| Goat anti-rabbit | Abcam | Biotin | ab6720 | 1:1000 | 2 h at RT for brain sections |
| Donkey anti-mouse | Jackson ImmunoResearch | Biotin | 715-065-151 | 1:1000 | 1 h at RT for cultured cells |
| Goat anti-rabbit | Jackson ImmunoResearch | AF647 | 111-605-144 | 1:500 | 1 h at RT for cultured cells |
| Goat anti-rabbit | Jackson ImmunoResearch | Cy3 | 111-165-008 | 1:500 | 2 h at RT for brain sections |
| Goat anti-rabbit | Jackson ImmunoResearch | AF488 | 111-545-144 | 1:500 | 2 h at RT for brain sections |
| Goat anti-mouse | Thermo Fisher scientific | AF488 | a11001 | 1:500 | 1 h at RT for cultured cells |
| Goat anti-rabbit | Thermo Fisher scientific | DNA HCR initiators | 31212 | 5 µg · mL$^{-1}$ | 2 h at RT for brain sections; 1 h at RT for Western blot and cultured cells |
| Goat anti-rat | Thermo Fisher scientific | DNA HCR initiators | 31220 | 5 µg · mL$^{-1}$ | 2 h at RT for brain sections; 1 h at RT for Western blot and cultured cells |

| Fluorescent reagents: | | | | | |
|---|---|---|---|---|---|
| Name | Vendor | Label | Cat. No. | Conc. | Incubation Time |
| Streptavidin-AF546 | Thermo Scientific | Alexa Fluor 546 | S-11225 | 1 µg · mL$^{-1}$, 1:500 | 1 h at RT for thin brain sections |
| Streptavidin-AF488 | Jackson ImmunoResearch | Alexa Fluor 488 | 016-540-084 | 1 µg · mL$^{-1}$, 1:500 | 1 h at RT |
| Streptavidin | Sigma-Aldrich | N.A. | S4762 | 1 µg · mL$^{-1}$, 1:500 | 30 min at RT for thin brain sections |

Example 1

The isHCR Method can Dramatically Amplify Immunofluorescent Signals in Various Types of Biological Samples.

Figure 1A:
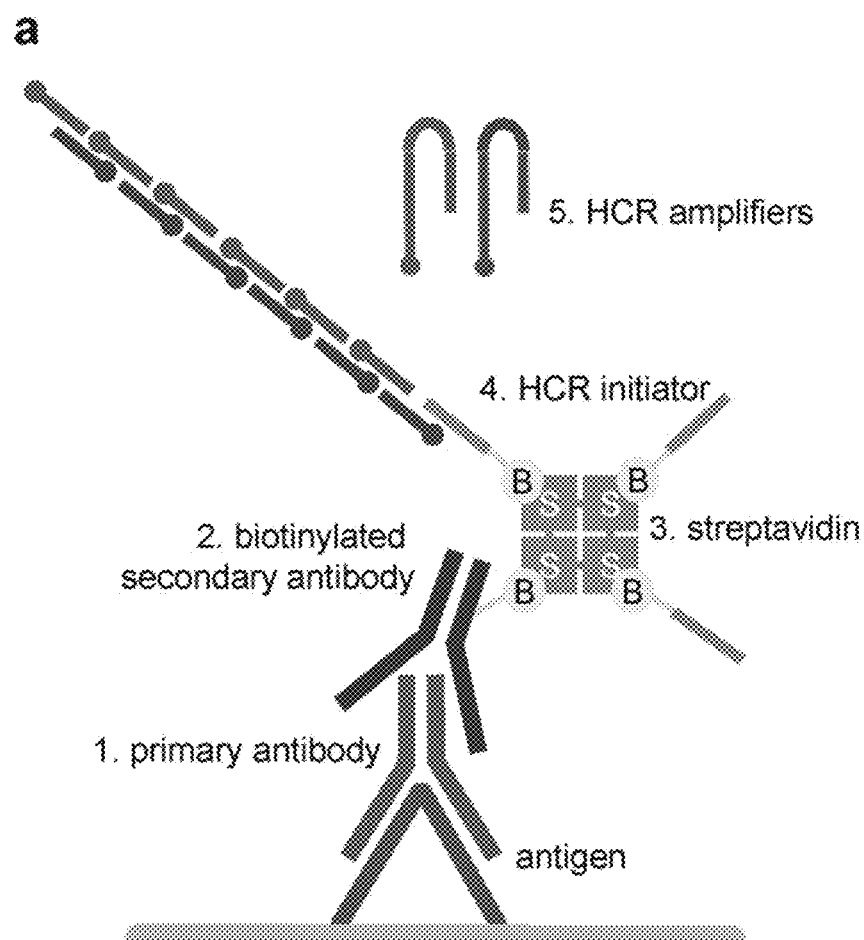
FIG. 1 The isHCR method can dramatically amplify immunofluorescent signals in various types of biological samples.
Figure 1B:
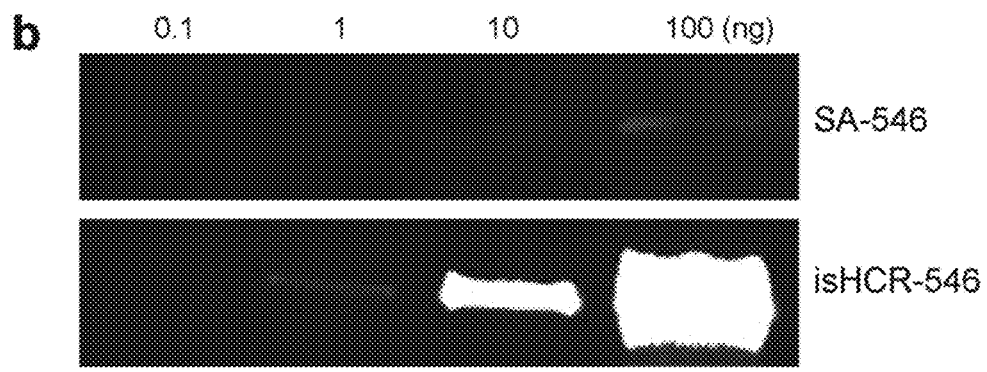
Figure 1C:
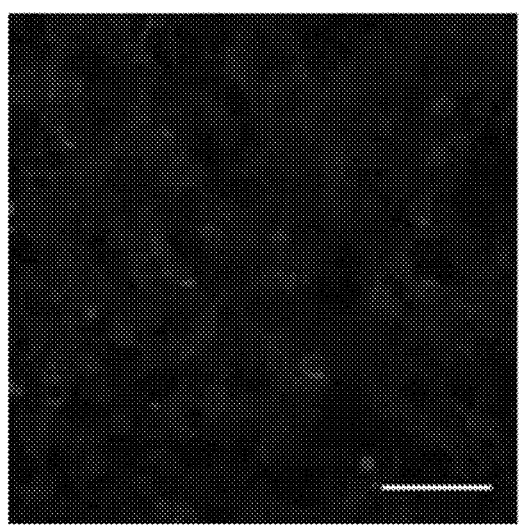
Figure 1C:
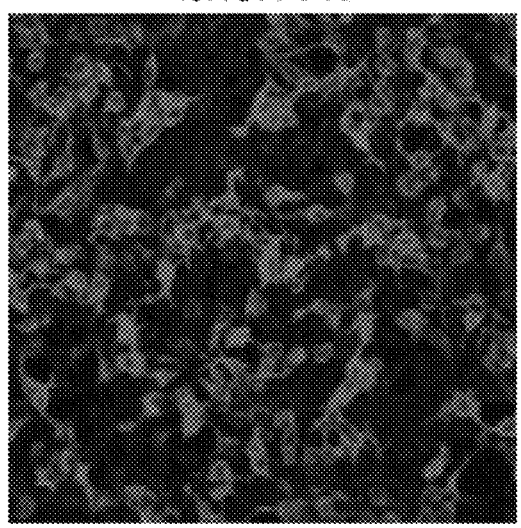
Figure 1D:
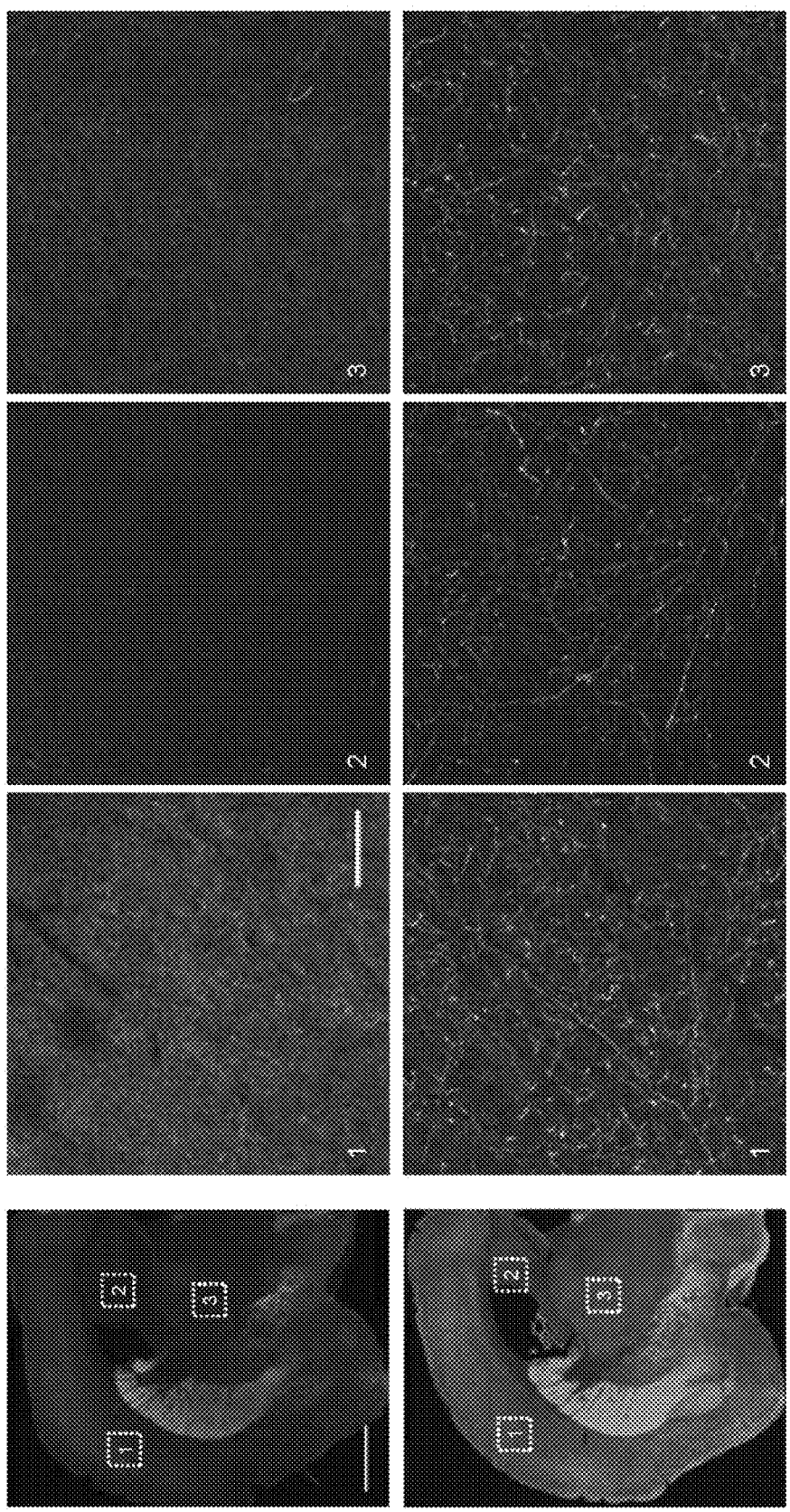
Figure 1E:
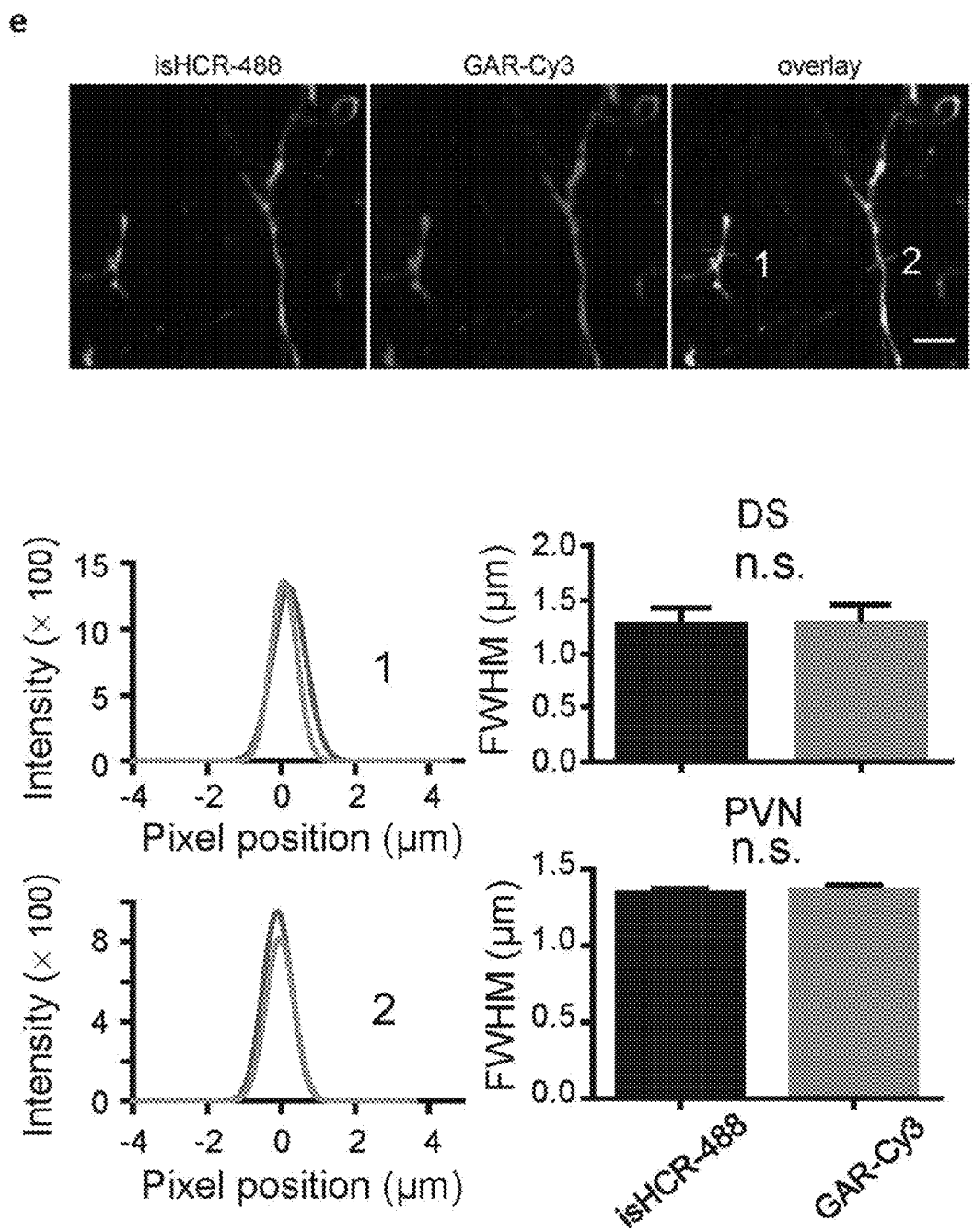
Figure 2A:
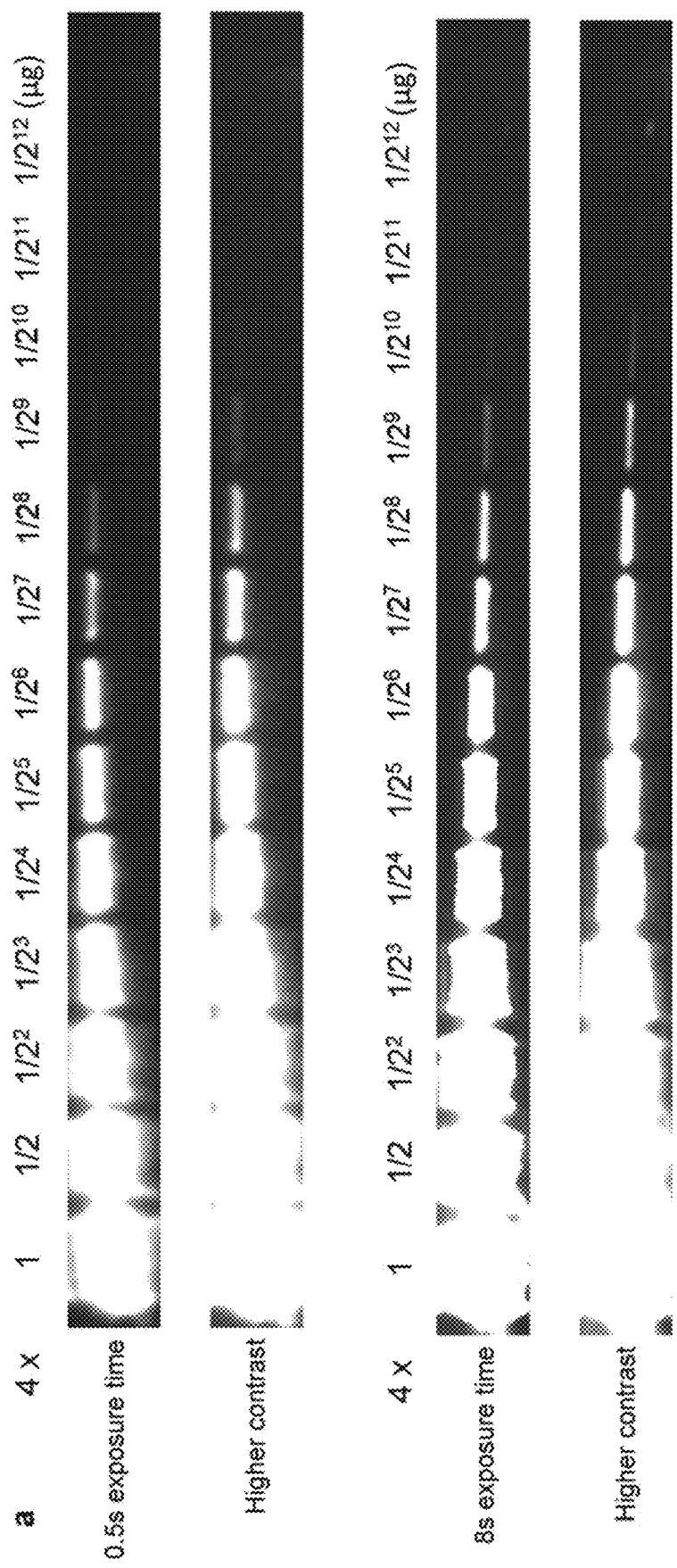
FIG. 2. Determining the dynamic range for Western blotting using isHCR. Purified scFv-GCN4-HA-GB1 protein was serially diluted.
Figure 2B:
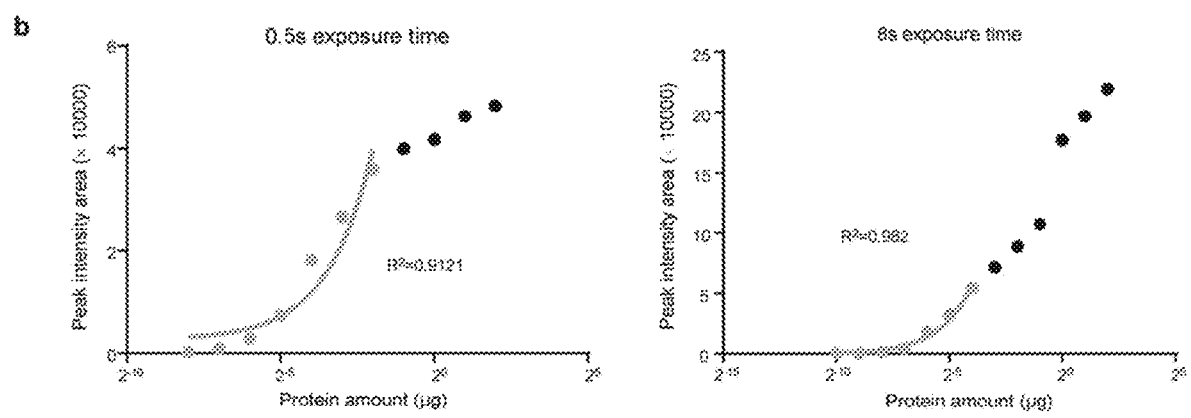
Figure 2C:
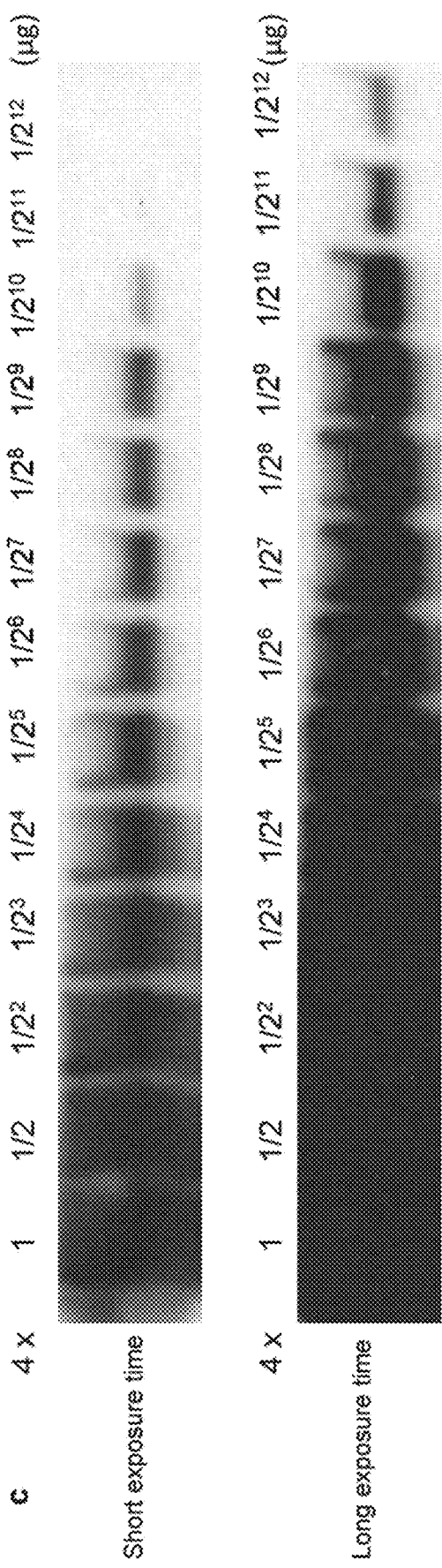
Figure 2D:
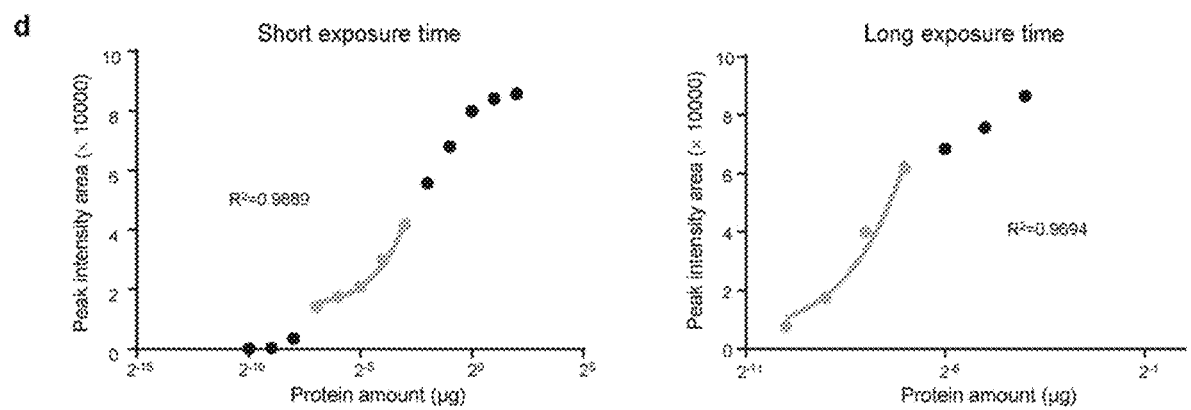

FIG. 1(a) shows schematic of the isHCR method using the biotin-streptavidin interaction. DNA-biotin HCR initiators are attached to antibodies and in turn trigger the self-assembly of DNA-fluorophore HCR amplifiers into fluorescent polymers. FIG. 1(b) shows validation with western blotting of purified scFv-GCN4-HA-GB, which was recognized by a biotinylated anti-HA primary antibody and visualized with Alexa Fluor 546-conjugated streptavidin (SA-546) or with Alexa Fluor 546-conjugated HCR amplifiers (isHCR-546). FIG. 1(c) shows that HEK293T cells expressing membrane-bound enhanced GFP (mGFP) were immunostained for GFP using a biotinylated anti-GFP antibody with SA-546 or isHCR-546. FIG. 1(d) shows images of mouse brain sections immunostained against TH using SA-488 (upper panels) or isHCR-488 (lower panels). Right panels show zoomed-in views of the boxed regions. In this and the following figures, the same imaging parameters were used for the comparison of the signal intensities from standard IHC methods and from isHCR, unless otherwise specified. FIG. 1(e) shows a mixture containing equal amounts of Cy3-conjugated secondary antibodies (GAR-Cy3, unamplified) and biotinylated secondary antibodies was used to detect the anti-TH primary antibodies. The signals of the biotinylated secondary antibodies were amplified using isHCR-488. The laser powers were adjusted to produce similar intensity profiles for the two channels. The width of TH-positive neuronal processes was measured using signals from either unamplified or isHCR-amplified channels. An example of two measured fibers is shown. No significant difference of the mean FWHM was observed in either the DS or the PVN (n=196, P=0.1069 for DS; n=256, P=0.8327 for PVN; paired t-test). Error bars indicate s.e.m. Scale bars, 100 µm (c, d right panel), 1 mm (d left panel), 10 µm (e).

Example 2

Determining the Dynamic Range for Western Blotting Using isHCR. Purified scFv-GCN4-HA-GB1 Protein was Serially Diluted.

FIG. 2 shows that the analyte proteins were recognized by a biotinylated anti-HA primary antibody and visualized with isHCR-546 (a) or a traditional HRP-ECL method (c). The peak intensity area of each lane was calculated and plotted using the signals acquired with short (up panels of a, c) and long (bottom panels of a, c) exposure time. The lanes that contained the lowest amount of analyte protein detected are highlighted in red color. The linear dynamic range using either detection method under each exposure time is plotted using a loge scale and highlighted in blue color (b, d). Note that the isHCR amplification method covers a dynamic range of 7 units (b), whereas the HRP-ECL method covers a range of 4 or 5 units depending on the exposure time (d).

Example 3 isHCR Amplification Maintains the Spatial Resolution of Membrane-Bound GFP (mGFP) Immunosignals in Cultured Cells.

Figure 3C:
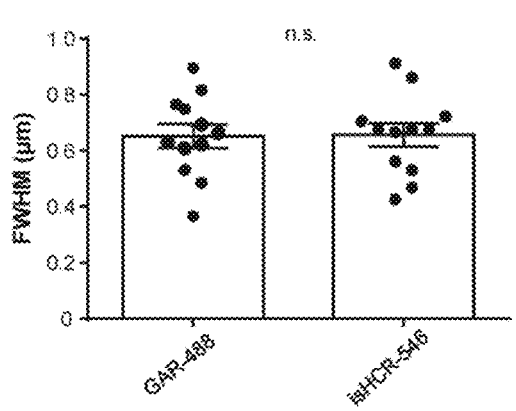

FIG. 3 shows that isHCR amplification maintains the spatial resolution of membrane-bound GFP (mGFP) immunosignals in cultured cells. FIG. 3(a) shows that mGFP proteins in HEK293T cells were immunostained and visualized using an antibody mixture that contained equal amounts of Alexa Fluor 488-conjugated secondary antibodies (GAR-488, green) and biotinylated secondary antibodies. The signals of biotinylated secondary antibodies were visualized using isHCR-546 (red). For comparison purpose, images were collected with different parameters to achieve similar intensity profiles for the two channels. FIG. 3(b) shows that a series of straight lines perpendicular to the membrane were drawn as illustrated for (a). The corresponding intensity profiles were plotted. The average intensity of each channel was calculated. The mean intensity of the distance from the cell edge (between −3 μm to −2 μm) was calculated as the baseline (denoted m). The peak value of the curve was determined (denoted p). Half-peak intensity (I) was defined (p+m)/2. The full width at half maximum (FWHM) was quantified as the width of the average intensity curve at I. FIG. 3(c) shows that no significant difference was observed between the FWHM calculated using the data from unamplified and isHCR-amplified samples (n=12; P=0.9163; paired t-test). Error bars indicate s.e.m. Scale bars, 10 μm.

Example 4

TH Immunostaining Using isHCR Reveals much Richer Catecholaminergic Innervations in the Brain.

FIG. 4 shows TH immunostaining using isHCR reveals much richer catecholaminergic innervations in the brain. FIG. 4(a) shows confocal images of the TH expression pattern in the VTA, the interpeduncular nucleus (IPN; upper panels), and the superior colliculus (lower panels) in mouse brain sections immunostained against TH using isHCR-488 or SA-488. FIG. 4(b) shows that no immunopositive signals were observed when we omitted the primary antibody. FIG. 4(c) shows images of mouse brain sections immunostained against TH using standard IHC and isHCR. A mixture containing equal amounts of Cy3-conjugated secondary antibodies (GAR-Cy3, unamplified) and biotinylated secondary antibodies was used to detect the anti-TH primary antibodies. The signals of the biotinylated secondary antibodies were amplified using isHCR-488. The signals of unamplified (red) and amplified (green) channels were colocalized. Note that we used different imaging parameters to achieve similar intensity profiles for the two channels. Scale bars, 100 μm (a, b), 50 μm (c).

Example 5

Optimization of isHCR that Reduces Background Noise.

FIG. 5 shows that optimization of isHCR reduces background noise. FIG. 5(a) shows the effect of unassembled HCR amplifiers and the addition of graphene oxide (GO) on the background fluorescence level after washing. FIG. 5(b) is a schematic showing that GO adsorbs the single-stranded overhang of HCR amplifiers and quenches the fluorescence of HCR amplifiers that are not assembled into double-stranded polymers. FIG. 5(c) shows in microplate wells, GO quenched the fluorescence of unassembled but not polymerized HCR amplifiers. In the bar plot, ns, not significant; *, P<0.05; ****, P<0.0001; t-test corrected for multiple comparisons using the Holm-Sidak method for analyzing the difference between each group (n=3 replicates). FIG. 5(d) shows images of the anterior cingulate cortex (ACC) in mouse brain sections immunostained against NeuN using isHCR-546 without GO or isHCR-546 with GO. The addition of GO significantly reduced the background signals and enhanced the signal-to-noise ratio (n=3; ns, not significant; *, P<0.05; ***, P<0.005; t-test). FIG. 5(e) shows images of the dorsal raphe nucleus in mouse brain sections immunostained against Vglut3 using SA-546, isHCR-546 without GO, or isHCR-546 with GO. Lower panels show zoomed-in views of boxed regions in the upper panels. The images of SA-546 samples were collected using higher pin hole values, detector gain settings, and laser intensities (higher settings). Error bars indicate s.e.m. in (c and e). Scale bars, 50 μm (a, d, e).

Example 6 isHCR Dramatically Increases IHC Signals in Mouse Brain Sections.

Figure 6A:
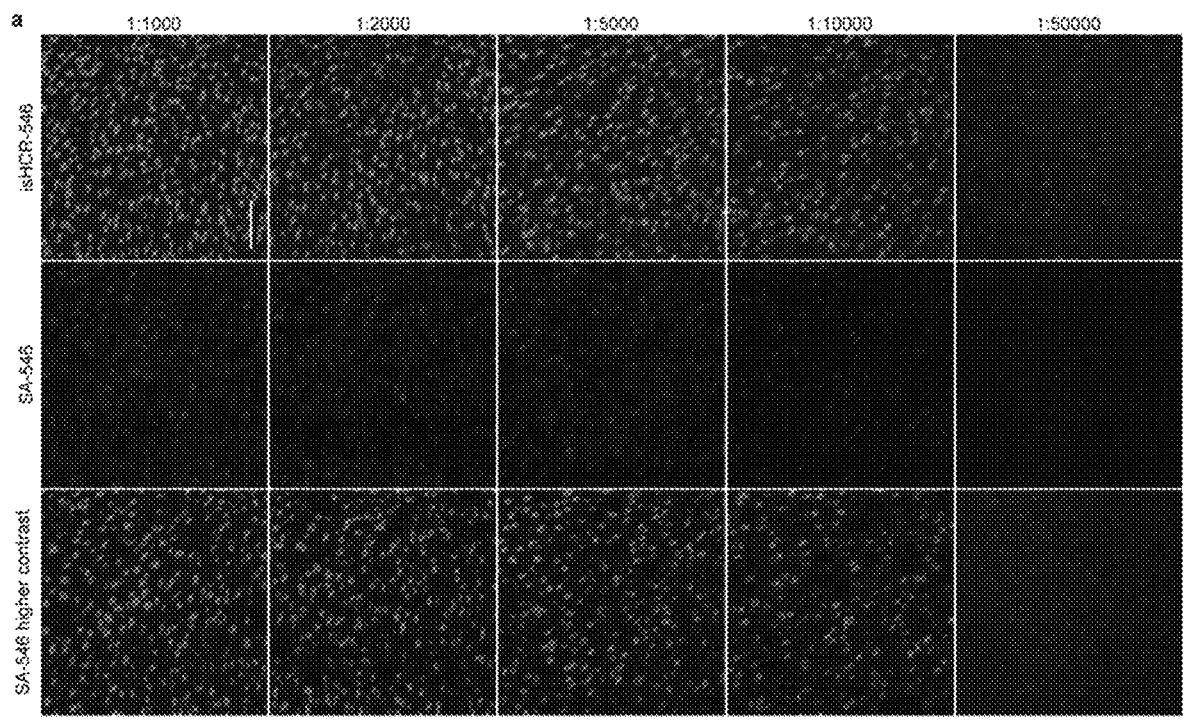
FIG. 6. isHCR dramatically increases IHC signals in mouse brain sections.
Figure 6B:
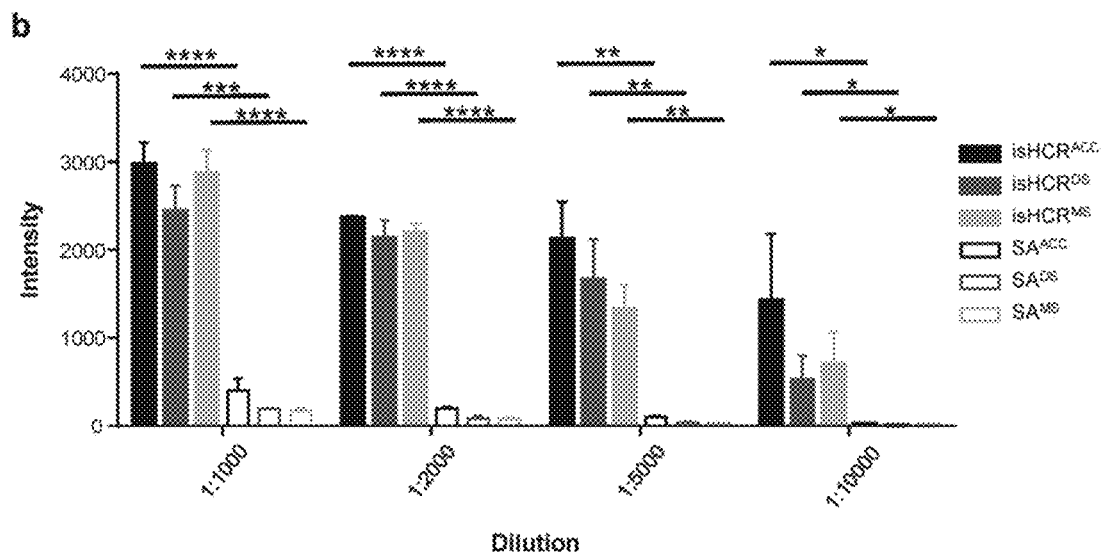
Figure 6C:
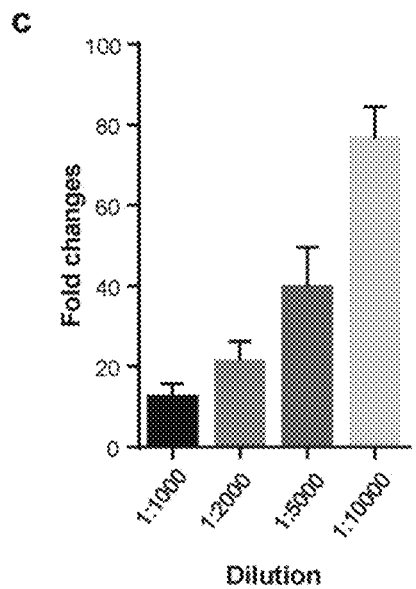

FIG. 6(a) shows that mouse brain sections were immunostained against NeuN. Parallel experiments were performed using anti-NeuN primary antibodies with different dilution ratios. The signals were visualized using isHCR-546 (top) or SA-546 (middle and bottom). The images of isHCR-546 and SA-546 samples from the ACC area were acquired using identical microscopy settings. Bottom panels show the higher contrast images of SA-546 samples. FIG. 6(b) shows the quantification of the signal intensity in three regions of the samples in FIG. 6(a). The signal intensity of isHCR-amplified samples was significantly higher than that of unamplified SA-546 samples. * P<0.05;  P<0.01; * P<0.001; **** P<0.0001; unpaired t-test. (c) The amplification factors of isHCR-546 vs. SA-546 at different antibody dilutions. Error bars indicate s.e.m. in (b and c). Scale bar, 100 μm.

Example 7 isHCR Specifically Amplifies Vglut3 Immunosignals in Mouse Brain Sections.

FIG. 7 shows that isHCR specifically amplifies Vglut3 immunosignals in mouse brain sections. FIG. 7(a) indicates confocal images of the medial raphe nucleus in mouse brain sections immunostained against Vglut3 using isHCR-546 or SA-546. For isHCR-546, graphene oxide (GO) was mixed with HCR amplifiers to quench the background fluorescence. FIG. 7(b) shows that no Vglut3-immunopositive signals were observed in brain sections with the primary antibody omitted (upper panel) or in the brain sections of Vglut3−/− mice immunostained using isHCR-546 (lower panel). FIG. 7(c) shows the quantification of data from brain section samples immunostained against Vglut3 using SA-546, isHCR546 without GO, or isHCR with GO (n=3 brain sections for each group; P<0.0001; Kolmogorov-Smirnov test). FIG. 7(d) shows comparison between isHCR and standard IHC. A mixture containing equal amounts of Alexa Fluor 488-conjugated secondary antibodies (GAR-488) and biotinylated secondary antibodies was used to detect the anti-Vglut3 primary antibodies. The signals of the biotinylated secondary antibodies were amplified using isHCR-546. The signals of unamplified (green) and amplified (red) channels were colocalized. FIG. 7(e) shows that the mean diameter of Vglut3-positive puncta was measured using the data from unamplified and isHCR-amplified samples. A representative measured punctum is shown. A straight line across the punctum was drawn and rotated using the punctum as the center of rotation. For every 6 degrees, the intensity profile along the line of both the unamplified and isHCR-amplified channel was plotted. The average intensity of each channel was calculated, and baseline correction was then applied. The corrected average intensity of each channel was fit to a Gaussian distribution with a non-linear least square method. FWHM was calculated with the equation: $FWHM=2\sqrt{2\ln 2}\sigma$, where $\sigma$ is the standard deviation of the fitted Gaussian curve. The results of FWHM for the two channels were compared. No difference of the mean diameter of Vglut3-positive puncta was observed (n=20; P=0.1846; paired t-test). Error bars indicate s.e.m. in (e). Scale bars, 100 μm (a, b), 50 μm (d), 10 μm (e).

Example 8 isHCR Effectively Amplifies Various Immunofluorescence Signals.

FIG. 8 shows that mouse brain sections were immunostained for (a) vasoactive intestinal peptide (VIP; a neuropeptide), (b) neuronal nitric oxide synthase (nNOS; a cytosolic enzyme), or (c) aromatic L-amino acid decarboxylase (AADC; an enzyme in axon terminals) using isHCR-546 or SA-546. Scale bars, 100 μm (a, b), 500 μm (c).

Example 9 isHCR Enables the Detection of Biomolecules that are Challenging for a Standard IHC Method.

FIG. 9(a) shows wide-field images of mouse brain sections immunostained against GAD67 using a biotinylated monoclonal primary antibody. The signals were visualized with isHCR-546 (top) or SA-546 (bottom). FIG. 9(b) indicates high-power confocal images showing GAD67 immunoreactivity in boxed areas in FIG. 9(a). The images of SA-546 and isHCR-546 samples were collected using identical microscopy settings. The right panels show images of the same regions in the middle panels collected using higher settings. FIG. 9(c) shows images of HeLa cells infected with *S. Typhimurium*. SteA-FLAG mutant strain (top and bottom) and wild-type strain (middle) were used. The detection of FLAG-tagged SteA was achieved using isHCR-488 (up). No specific signal was observed using a standard IHC method (unamplified, Donkey anti-mouse, DAM-488, bottom) or in HeLa cells samples infected with wild-type *S. Typhimurium* (middle). Scale bars, 1 mm (a), 100 μm (b), 10 μm (c).

Example 10 isHCR Amplification Enables the Detection of Low-Abundance Proteins.

Figure 10C:
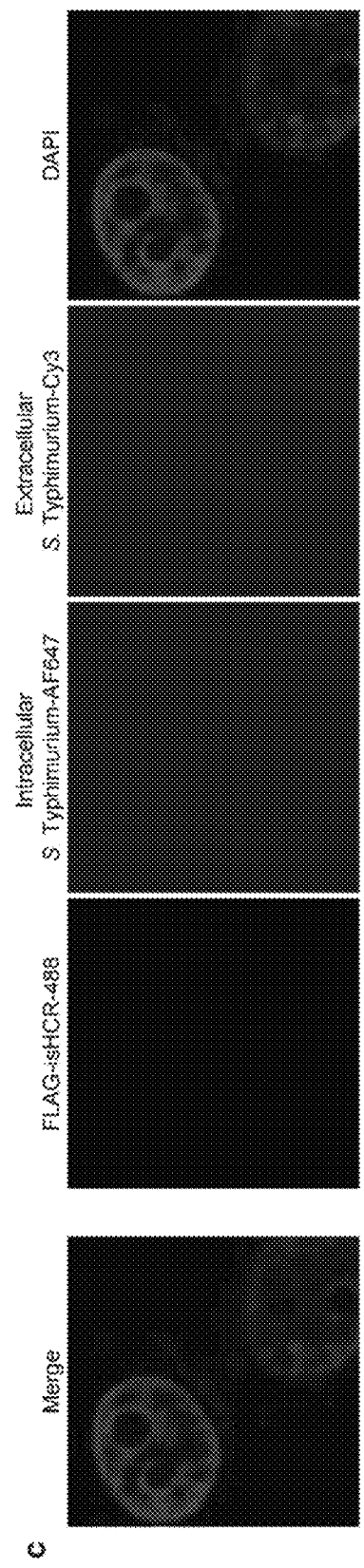

FIG. 10 shows that isHCR amplification enables the detection of low-abundance proteins. FIG. 10(a) shows images of mouse brain sections immunostained against c-Fos using a monoclonal antibody. The signals were visualized using isHCR-546 or SA-546. The left panel shows the images of the mice that explored the enriched environment. The right panel shows the images of the control mice that were not allowed to explore the enriched environment. FIG. 10(b) shows images of HeLa cells infected with SopD2-FLAG *S. Typhimurium* mutant strain. The detection of FLAG-tagged SopD2 was achieved using isHCR-488 (up) but not the standard IHC using Alexa Fluor 488-labeled secondary antibody (unamplified, Donkey anti-mouse, DAM-488, bottom). FIG. 10(c) shows that no specific signal was detected in HeLa cells that were not infected by *S. Typhimurium*. Scale bar, 50 μm (a), 10 μm (b, c).

Example 11

HCR Initiators can be Conjugated Directly onto Antibodies Using Chemical Linkers.

Figure 11A:
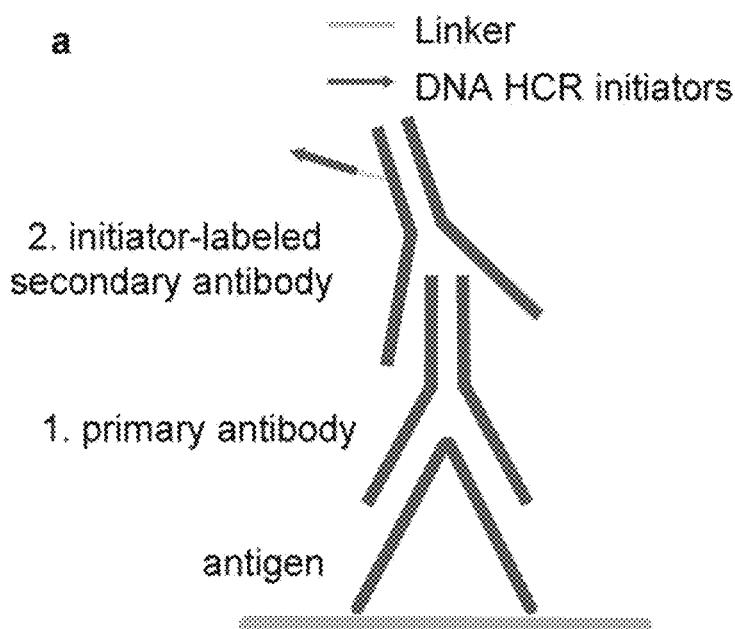
FIG. 11. HCR initiators can be conjugated directly onto antibodies using chemical linkers.
Figure 11B:
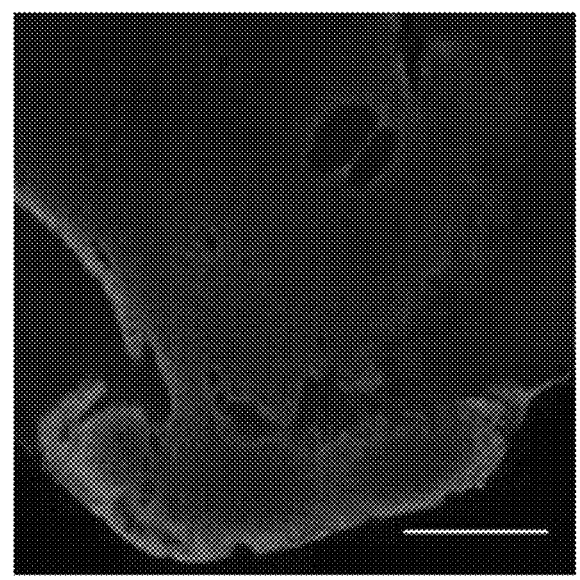
Figure 11C:
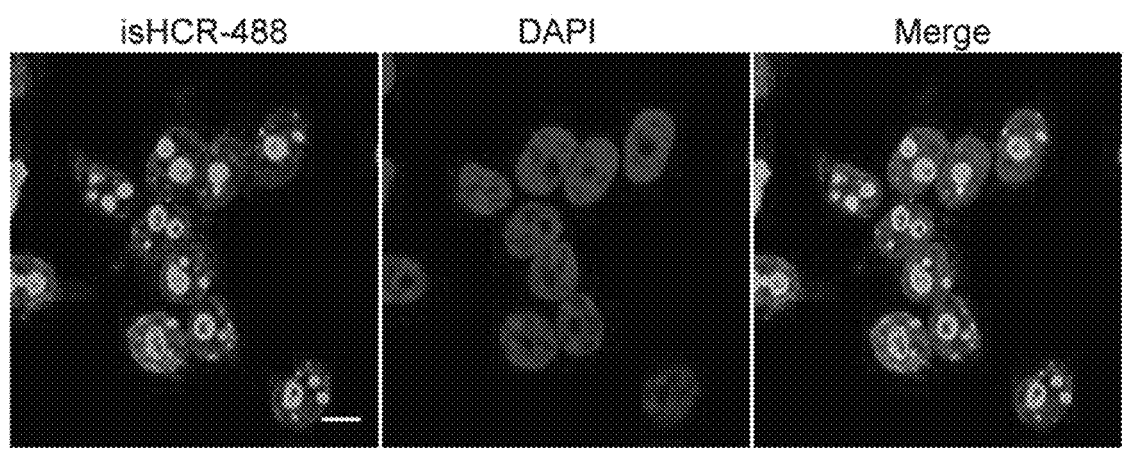

FIG. 11(a) shows schematic of the direct conjugation of HCR initiators and IgGs. FIG. 11(b) shows mouse brain sections immunostained against DAT using HCR initiator-conjugated secondary antibodies. The HCR initiators were conjugated onto antibodies using SMCC as linkers. The signals were amplified using isHCR-546. FIG. 11(c) shows images of HEK 293T cells immunostained against the nuclear protein Ki67 using HCR initiator-conjugated secondary antibodies. The HCR initiators were conjugated onto antibodies using NHS-Azide as linkers. The signals were amplified using isHCR-488. Scale bar, 500 μm (b), 10 μm (c).

Experimental Results

As shown in Table 3, the present isHCR using various reagents, antibodies and amplifier with different modification not only dramatically enhances the detection of analyte proteins in western blotting, but also dramatically enhances the performance of IHC in cultured cell samples and in tissue section samples. In addition, the present improved isHCR with GO achieves high-level amplification with low background noise in IHC in tissue section samples. In particular, the present improved isHCR with GO significantly enhances the detection of a vesicular transporter, successfully enhances various immunofluorescence signals, dramatically enhances the performance of monoclonal antibodies in IHC, and enables the detection of bacterial effectors that are translocated in vivo.

TABLE 3

Summary of Experimental Results

| Antibodies and Reagents used in Examples | Figures and Examples | Effects and Results |
|---|---|---|
| Streptavidin, Streptavidin-AF546, B1 I2, B1 Amplifier H1 546, B1 Amplifier H2 546, anti-HA antibody | FIG. 1b and FIG. 2 (Examples 1 and 2) | isHCR dramatically enhances the detection of analyte proteins in western blotting. |

TABLE 3-continued

Summary of Experimental Results

| Antibodies and Reagents used in Examples | Figures and Examples | Effects and Results |
|---|---|---|
| Streptavidin, Streptavidin-AF546, B1 I2, B1 Amplifier H1 546, B1 Amplifier H2 546, anti-GFP antibody, biotinylated goat anti-rabbit antibody, AF488-goat anti-rabbit antibody | FIG. 1c and FIG. 3. (Examples 1 and 3) | isHCR dramatically enhances the performance of IHC in cultured cell samples. |
| Streptavidin, Streptavidin-AF546, B1 I2, B1 Amplifier H1 546, B1 Amplifier H2 546, B5 I2, B5 Amplifier H1 488, B5 Amplifier H2 488, anti-TH antibody, biotinylated goat anti-rabbit antibody, Cy3-goat anti-rabbit antibody | FIG. 1d, e and FIG. 4 (Examples 1 and 4) | isHCR dramatically enhances the performance of IHC in tissue section samples. |
| B1 I2, B1 Amplifier H1 546, B1 Amplifier H2 546, GO | FIG. 5a, c (Example 5) | GO significantly reduces the background signals of isHCR amplification. |
| Streptavidin, Streptavidin-AF546, B1 I2, B1 Amplifier H1 546, B1 Amplifier H2 546, anti-NeuN antibody, GO, biotinylated goat anti-rabbit antibody | FIG. 2d and FIG. 6 (Examples 2 and 6) | The improved isHCR with GO achieves high-level amplification with low background noise in IHC in tissue section samples. |
| Streptavidin, Streptavidin-AF546, B1 I2, B1 Amplifier H1 546, B1 Amplifier H2 546, anti-Vglut3 antibody, GO, biotinylated goat anti-rabbit antibody, AF488-goat anti-rabbit antibody | FIG. 5e and FIG. 7 (Examples 5 and 7) | The improved isHCR with GO significantly enhances the detection of a vesicular transporter (Vglut3), which is difficult for traditional IHC method. |
| Streptavidin, Streptavidin-AF546, B1 I2, B1 Amplifier H1 546, B1 Amplifier H2 546, GO, anti-VIP antibody, anti-AADC antibody, anti-nNOS antibody, biotinylated goat anti-rabbit antibody | FIG. 8 (Example 8) | The improved isHCR with GO successfully enhances various immunofluorescence signals. |
| Streptavidin-AF546, B1 I2, B1 Amplifier H1 546, B1 Amplifier H2 546, GO, anti-GAD67 antibody, anti-c-Fos antibody, biotinylated donkey anti-mouse antibody. | FIG. 9a and FIG. 10a (Examples 9 and 10) | The improved isHCR with GO dramatically enhances the performance of monoclonal antibodies in IHC. |
| Streptavidin, Streptavidin-AF546, B1 I2, B1 Amplifier H1 546, B1 Amplifier H2 546, GO, anti-FLAG antibody, anti-*Salmonella* antibody, biotinylated donkey anti-mouse antibody, Cy3-goat anti-rabbit antibody, AF647-goat anti-rabbit antibody, AF488-anti-mouse antibody. | FIG. 9c and FIG. 10b, c (Examples 9 and 10) | The improved isHCR with GO enables the detection of bacterial effectors that are translocated in vivo. |
| Goat anti-rabbit antibody, Goat anti-rat antibody, SMCC linker, NHS-azide linker, B1 I2 Thiol, B5 I2 Thiol, B1 I2 DBCO, B5 I2 DBCO | FIG. 11 (Example 11) | The direct conjugation of isHCR initiators with IgGs through chemical linkers allows rapid amplification of immunosignals |
| Streptavidin, Goat anti-rat antibody, anti-substance P antibody, B1 Amplifier H1 Terminal Biotin, B1 Amplifier H2 Terminal Biotin, B1 Amplifier H1 Internal Biotin, B1 Amplifier H2 Internal Biotin, B1 Amplifier H1 Internal Biotin and 5'-488, B1 Amplifier H2 Internal Biotin and 3'-488, B1 Amplifier H1 546, B1 Amplifier H2 546, B1 I2 | FIG. 12 (Example 12) | Multi-round amplification using isHCR$^n$ |

Example 12

Multi-Round Amplification Using isHCR$^n$.

FIG. 12(a) shows schematic overview of isHCR$^n$. The initial and branching rounds use DNA-biotin HCR amplifiers for additional attachment of HCR initiators. The final round uses DNA-fluorophore HCR amplifiers to visualize the signals. (b) Western blots of purified scFv-GCN4-HA-GB1 protein after one or three rounds of isHCR (isHCR$^1$ vs. isHCR$^3$). (c) In order to evaluate the accessibility of biotin groups on the amplification polymers, we performed immunostaining against TH on brain sections using isHCR$^n$. We tested the performance of two pairs of amplifiers with biotin attached at either an internal or the terminal site. After each round of amplification, SA-546 was applied to detect the biotin groups. Tagging biotin at the internal position led to substantially higher amplification efficiency than at the terminal site. (d) Mouse brain sections were immunostained against TH. The signals were first amplified by isHCR using biotin and Alexa-fluor-488 dual-labeled HCR amplifiers, and then further amplified by an additional round of isHCR using Alexa-fluor-546 labeled HCR amplifiers. The signals of the first and second round of amplification were colocalized. We used different imaging parameters to achieve similar intensity profiles for the two channels. (e) The width of TH-positive neuronal processes was measured using signals from either isHCR$^1$-488 or isHCR$^2$-546 channels. An example of a measured fiber is shown. No significant difference of the mean FWHM was observed (n=50; P=0.7119; paired t-test). (f) Images of mouse brain slices immunostained against substance P without amplification (SA-546) or with 1-3 rounds of amplification (isHCR$^1$-546, isHCR$^2$-546, and isHCR$^3$-546). (g) Mouse brain sections were immunostained against substance P using isHCR$^3$. Multi-round amplification by isHCR$^3$ revealed a patchy distribution of substance P in the striatum. The right panel shows the zoomed-in image of the boxed region at the left. Error bars indicate s.e.m. in (e). Scale bars, 500 μm (c, f, g left), 100 μm (g right), 50 μm (d), 10 μm (e).

The invention claimed is:

1. An immunosignal Hybridization Chain Reaction (isHCR), which comprises conjugating a hybridization chain reaction (HCR) initiator to an antibody specific to an analyte, and adding a pair of HCR amplifiers to conduct a hybridization chain reaction, wherein an amplifier or a pair of amplifiers are modified to perform branched multiple-round amplification in order to branch and grow HCR polymers, and the amplifier or the pair of amplifiers are internally modified with a chemical group and/or a fluorescent dye which initiates further rounds of amplification.

2. The immunosignal Hybridization Chain Reaction of claim 1, wherein the HCR initiator has a region for hybridizing with a HCR amplifier, and a region for conjugating an antibody specific to an analyte.

3. The immunosignal Hybridization Chain Reaction of claim 1, wherein the HCR initiator is terminally modified and/or internally modified with biotin, acrydite, amine, thiol, DBCO, and/or fluorescent dye, and the fluorescent dye is selected from Cyanine dyes, coumarin dyes, fluorescein dyes, and rhodamine dyes; and/or
the amplifier is terminally modified and internally modified with biotin, acrydite, amine, thiol, DBCO, and/or fluorescent dye, and the fluorescent dye is selected from Cyanine dyes, coumarin dyes, fluorescein dyes, and rhodamine dyes.

4. The immunosignal Hybridization Chain Reaction of claim 1, wherein the HCR initiator is conjugated to an antibody via an interaction selected from streptavidin-biotin interaction and covalent bond interaction.

5. The immunosignal Hybridization Chain Reaction of claim 4, wherein the HCR initiator is a biotinylated initiator, which is capable of attaching to the vacant binding sites of streptavidin, and the streptavidin is capable of attaching to a biotinylated antibody, and whereby the HCR initiator is conjugated to the antibody.

6. The immunosignal Hybridization Chain Reaction of claim 4, wherein the covalent bond interaction is an interaction via a chemical linker selected from an amine-reactive linker containing a succinimidyl ester group and a click chemistry linker.

7. The immunosignal Hybridization Chain Reaction of claim 6, wherein the click chemistry linker is selected from NHS-Azide linker, NHS-DBCO linker, maleimide-azide linker, and maleimide-DBCO linker.

8. The immunosignal Hybridization Chain Reaction of claim 1 wherein the said chemical group is selected from biotin, digoxigenin, acrydite, amine, succinimidyl ester, thiol, azide, TCO, Tetrazine, Alkyne, and/or DBCO, and the said fluorescent dye is selected from Cyanine dyes, coumarin dyes, fluorescein dyes, and rhodamine dyes.

9. The immunosignal Hybridization Chain Reaction of claim 1, wherein a pair of fluorophore-tagged amplifiers are added to a final round of the branched multiple-round amplification for visualization.

10. The immunosignal Hybridization Chain Reaction of claim 1, wherein the amplifiers are modified at internal positions, which are accessible to streptavidins, which serve as anchors for each successive round of branching in multi-round isHCR.

11. The immunosignal Hybridization Chain Reaction of claim 1, wherein the antibody is a IgG, a Single-domain $V_HH$ antibody or a scFv.

12. The immunosignal Hybridization Chain Reaction of claim 1, further comprising using grapheme oxide (GO) for absorbing unassembled HCR amplifiers; or further comprising using grapheme oxide (GO) for absorbing unassembled HCR amplifiers and quenching the fluorescence, wherein the amplifiers are internally modified with fluorescent dye or the amplifiers are terminally modified and internally modified with fluorescent dye, wherein GO has a particle size of <500 nm.

13. A method for amplifying immunosignal, for analyzing an analyte in a biological sample, or for laboratory, clinical or diagnostic application, comprising performing the immunosignal Hybridization Chain Reaction of claim 1.

14. The method of claim 13, wherein the clinical or diagnostic application is selected from biological research, forensic examination, clinical tests or diagnosis, Western blotting and ELISA.

15. The method of claim 13, wherein the biological sample is selected from cultured cell, dissociated cell, tissue section, body fluid, and whole organ.

16. A kit for an immunosignal Hybridization Chain Reaction (isHCR), comprising: (1) an antibody specific to an analyte; (2) a HCR initiator; and (3) a pair of HCR amplifiers, wherein the HCR initiator has a region for hybridizing with a HCR amplifier, and a region for conjugating the antibody, wherein an amplifier or a pair of amplifiers are internally modified with a chemical group and/or a fluorescent dye.

17. The kit of claim 16, wherein the HCR initiator is terminally modified and/or internally modified with biotin, acrydite, amine, thiol, DBCO, and/or fluorescent dye, and said fluorescent dye is selected from Cyanine dyes, coumarin dyes, fluorescein dyes, and rhodamine dyes; and/or the amplifier is terminally modified and internally modified with biotin, acrydite, amine, thiol, DBCO, and/or fluorescent dye; preferably, wherein the HCR initiator is conjugated to an antibody via an interaction selected from streptavidin-biotin interaction and covalent bond interaction, wherein the HCR initiator is a biotinylated initiator, which is capable of attaching to the vacant binding sites of streptavidin, and the streptavidin is capable of attaching to a biotinylated antibody, and whereby the HCR initiator is conjugated to the antibody, and wherein the covalent bond interaction is an interaction via a chemical linker selected from an amine-reactive linker containing a succinimidyl ester group and a click chemistry linker.

18. The kit of claim 17, wherein the click chemistry linker is selected from NHS-Azide linker, NHS-DBCO linker, maleimide-azide linker, and maleimide-DBCO linker.

19. The kit of claim 16, wherein the chemical group selected from biotin, digoxigenin, acrydite, amine, succinimidyl ester, thiol, azide, TCO, Tetrazine, Alkyne, and/or DBCO; and/or the fluorescent dye selected from Cyanine dyes, coumarin dyes, fluorescein dyes, and rhodamine dyes.

20. The kit of claim 16, wherein antibody is a IgG, a Single-domain $V_HH$ antibody or a scFv.

21. The kit of claim 16, further comprising grapheme oxide (GO) for absorbing unassembled HCR amplifiers; or further comprising grapheme oxide (GO) for absorbing unassembled HCR amplifiers and quenching the fluorescence.

* * * * *